(12) United States Patent
Kupersmith et al.

(10) Patent No.: US 11,302,450 B2
(45) Date of Patent: Apr. 12, 2022

(54) COMPUTER-IMPLEMENTED SYSTEM AND METHOD FOR GUIDED ASSESSMENTS ON MEDICATION EFFECTS

(71) Applicant: SafeTherapeutics, LLC, New York, NY (US)

(72) Inventors: Mark Kupersmith, New York, NY (US); Dana Kupersmith, New York, NY (US); Karl Kieburtz, Middleburg, VA (US); Thomas Michael Chester, Shalimar, FL (US)

(73) Assignee: Safe Therapeutics, LLC, New York, NY (US)

( * ) Notice: Subject to any disclaimer, the term of this patent is extended or adjusted under 35 U.S.C. 154(b) by 438 days.

(21) Appl. No.: 16/372,902

(22) Filed: Apr. 2, 2019

(65) Prior Publication Data
US 2019/0304604 A1 Oct. 3, 2019

Related U.S. Application Data

(60) Provisional application No. 62/651,414, filed on Apr. 2, 2018.

(51) Int. Cl.
*G16H 70/40* (2018.01)
*G16H 50/20* (2018.01)
(Continued)

(52) U.S. Cl.
CPC ........ *G16H 70/40* (2018.01); *G06F 16/903* (2019.01); *G06F 40/20* (2020.01); *G06F 40/205* (2020.01);
(Continued)

(58) Field of Classification Search
None
See application file for complete search history.

(56) References Cited

U.S. PATENT DOCUMENTS 7,957,983 B2  6/2011  Hoffman et al.
9,218,457 B2  12/2015  Jackson et al.
(Continued)

FOREIGN PATENT DOCUMENTS

WO   WO-2017042396 A1 *  3/2017  ........... G06F 16/951

OTHER PUBLICATIONS

Sean Tracy, Search-Engine Data Gives Early Warnings of Drug Side Effects, Wired Sciencenow, https://www.wired.com/2013/03/google-side-effects/ (last visited Nov. 18, 2021) (Year: 2013).*

*Primary Examiner* — Elaine Gort
*Assistant Examiner* — Nicholas Akogyeram, II
(74) *Attorney, Agent, or Firm* — Finnegan, Henderson, Farabow, Garrett & Dunner LLP

(57) ABSTRACT

A system for identifying secondary effects of medications. The system may include one or more processors and a storage medium. The storage medium may stores instructions that configure the processors to perform operations. As configured, the processors may retrieve records associated with medications from servers. The processors may also extract machine readable content from records and identify portions that are associated with secondary effects of medications. Further, the processors may aggregate identified portions in a database, determine a level of evidence for records based on sources, associate records with metadata indicating the level of evidence; and generate index files mapping the markup language files, the metadata tags, and the medications. Moreover, the processor may receive search queries from a client, identify a subset of the records associated with medications in the query using index files, and transmit the identified subset ranked according to the level of evidence.

20 Claims, 21 Drawing Sheets

(51) Int. Cl.
*G16H 20/10* (2018.01)
*G16H 50/70* (2018.01)
*G16H 10/60* (2018.01)
*G06F 16/24* (2019.01)
*G06F 16/903* (2019.01)
*G06F 16/953* (2019.01)
*G06K 9/62* (2022.01)
*G06F 40/205* (2020.01)
*G06F 40/20* (2020.01)

(52) U.S. Cl.
CPC ......... *G06K 9/6223* (2013.01); *G06K 9/6267* (2013.01); *G16H 10/60* (2018.01); *G16H 20/10* (2018.01); *G16H 50/20* (2018.01); *G16H 50/70* (2018.01)

(56) References Cited

U.S. PATENT DOCUMENTS

| | | | |
|---|---|---|---|
| 9,372,895 B1* | 6/2016 | Zamansky | G06F 16/3322 |
| 2002/0165845 A1* | 11/2002 | Gogolak | G16C 20/30 |
| 2007/0088664 A1* | 4/2007 | Nakano | G16H 20/10 |
| | | | 706/10 |
| 2007/0112777 A1* | 5/2007 | Field | G06F 16/9537 |
| 2009/0106603 A1* | 4/2009 | Dilman | G06F 11/327 |
| | | | 714/42 |
| 2009/0240635 A1* | 9/2009 | Qian | G06Q 99/00 |
| | | | 705/500 |
| 2013/0082581 A1* | 4/2013 | Bufalini | G07F 17/0092 |
| | | | 312/209 |
| 2013/0096938 A1* | 4/2013 | Stueckemann | G16H 15/00 |
| | | | 705/2 |
| 2013/0179138 A1 | 7/2013 | Jackson et al. | |
| 2013/0179187 A1 | 7/2013 | Jackson et al. | |
| 2014/0330594 A1* | 11/2014 | Roberts | G06Q 10/06316 |
| | | | 705/4 |
| 2016/0078182 A1* | 3/2016 | Allen | G16H 50/30 |
| | | | 702/19 |
| 2016/0094491 A1* | 3/2016 | Fedorov | H04L 12/56 |
| | | | 709/206 |
| 2016/0140305 A1* | 5/2016 | Takeyama | G16H 10/60 |
| | | | 705/3 |
| 2016/0217395 A1 | 7/2016 | Tatonetti et al. | |
| 2016/0292367 A1 | 10/2016 | Tharpe et al. | |
| 2017/0076046 A1* | 3/2017 | Barnes | G06Q 10/06 |
| 2018/0068083 A1* | 3/2018 | Cohen | G16B 40/20 |
| 2018/0121605 A1* | 5/2018 | Allen | G16H 50/20 |
| 2018/0226143 A1* | 8/2018 | Khashman | G16H 10/60 |
| 2018/0336318 A1* | 11/2018 | Bhatt | G16H 50/20 |
| 2018/0365380 A1* | 12/2018 | Limsopatham | G16H 50/70 |
| 2019/0259482 A1* | 8/2019 | Puirava | G06N 20/00 |

* cited by examiner

Case No. 12323

1. Action taken with Med  ☐ Stopped  ☑ Reduced  ☐ Unchanged
2. Outcome of the problem  ☑ Improved  ☐ Worsened
3. If therapy changed, how long till condition improved?
   <u>6</u>  ⦿ Hrs  ○ Days  ○ Weeks Additional Comments Thank you for the feedback!

[Submit Feedback] — 2110

2102, 2104, 2106, 2108

COMPUTER-IMPLEMENTED SYSTEM AND METHOD FOR GUIDED ASSESSMENTS ON MEDICATION EFFECTS

CROSS-REFERENCE TO RELATED APPLICATIONS

This application claims the benefit of priority of U.S. Provisional Application No. 62/651,414, filed Apr. 2, 2018. The disclosure of the above-referenced application is expressly incorporated herein by reference to its entirety.

TECHNICAL FIELD

The present disclosure relates generally to systems and methods for providing guided assessments to resolve client device queries, and more particularly, to an artificial intelligence system that generates a database with easily accessible information based on disparate data sources, including client device queries, to provide guided assessments on medication adverse effects.

BACKGROUND

Identifying secondary effects of medications (whether harmful, unharmful, or beneficial)—such as adverse, abnormal, and/or unexpected effects—is complex and expensive. Although medications may be extensively tested before they are offered to the public, secondary effects (sometimes referred to as side effects) may only be discovered after trials when the medication is used for treatment. For example, some secondary effects only present themselves after long periods of use. Some may not be discovered during trials; and some cannot be discovered during trials. Also, certain secondary effects may not be monitored or tested during trials and they may only be identified when patients who are susceptible to the secondary effects use the medication. Therefore, it is informative and helpful to monitor for potential secondary effects of medications even after trials for marketing approval have been completed.

Physicians and medication manufacturers interested in monitoring secondary effects of medications face important challenges. For example, it can be difficult to establish correlations, let alone causal relationships, between a medication and a patient's condition. Particularly, after clinical trials, it can be challenging to isolate variables to identify correlations when circumstances are no longer tightly controlled and symptoms are not systematically evaluated. In addition, the relevant data are contained in many disparate sources, which are not aggregated and normalized.

The disclosed computer-implemented system and identification methods address one or more of the shortcomings set forth above and/or other shortcomings in the art.

SUMMARY

One aspect of the present disclosure is directed to a system for identifying secondary effects of prescribed medications. The system may include one or more processors and a storage medium. The storage medium stores instructions that, when executed, configure the one or more processors to perform operations. As configured, the processors may retrieve a plurality of records associated with medications from a plurality of servers. The processors may also extract machine readable content from each of the plurality of records and identify portions of the machine readable content that are associated with secondary effects of medications. Further, the processors may aggregate the identified portions of the machine readable content in a database using markup language files, determine a 'level of evidence' for each of the plurality of records based on corresponding record sources, associate each of the plurality records with metadata tags indicating the level of evidence; and generate index files mapping the markup language files, the metadata tags, and the medications. Moreover, the processor may receive a search query from a client device (the search query including at least one medication), identify a subset of the plurality of records associated with the at least one medication using the index files, and transmit, to the client device, the identified subset ranked according to the level of evidence.

Another aspect of the present disclosure is directed to a non-transitory computer-readable medium storing instructions that, when executed by a processor, cause the processor to operate a system for identifying secondary effects of medications. The operations may configure the processor to retrieve a plurality of records associated with medications from a plurality of servers. The processors may also extract machine readable content from each of the plurality of records and identify portions of the machine readable content that are associated with secondary effects of medications. Further, the processors may aggregate the identified portions of the machine readable content in a database using markup language files, determine a level of evidence for each of the plurality of records based on corresponding record sources, associate each of the plurality records with metadata tags indicating the level of evidence; and generate index files mapping the markup language files, the metadata tags, and the medications. Moreover, the processor may receive a search query from a client device (the search query including at least one medication), identify a subset of the plurality of records associated with the at least one medication using the index files, and transmit, to the client device, the identified subset ranked according to the level of evidence.

Yet another aspect of the present disclosure is directed to a computer-implemented method for identifying secondary effects of medications. The method may include operations of retrieving a plurality of records associated with medications from a plurality of servers and extracting machine readable content from each of the plurality of records. The method may also include identifying portions of the machine readable content that are associated with secondary effects of medications, aggregating the identified portions of the machine readable content in a database using markup language files, determining a level of evidence for each of the plurality of records based on corresponding record sources, associating each of the plurality records with metadata tags indicating the level of evidence, and generating index files mapping the markup language files, the metadata tags, and the medications. Further, the method may include operations of receiving a search query from a client device (the search query including at least one medication), identifying a subset of the plurality of records associated with the at least one medication using the index files, and transmitting, to the client device, the identified subset ranked according to the level of evidence.

Another aspect of the present disclosure is directed to a system including: a unique search, based on either patient symptoms or provider diagnoses regarding adverse health states; a complete, updated and secured database derived and synthesized from medical and scientific literature and FDA databases; coding systems of adverse health states that are standard in the medication development and marketing industries, clinical trials, and global health organizations. The system may additionally include existing marketed and in-development (with human testing reported) prescription and over the counter medications.

Yet another aspect of the present disclosure is directed to a computer-implemented product outputting information about correlations between medications and secondary effects. The computer-implemented product may include a summary of the associations identified, with links to specific data sources from the medical literature and FDA. For example, the product may include graphical user interfaces with URLs referencing articles or a links to a specific documents. In such embodiments, the computer-implemented product may include information that may be prioritized and labeled by the level of evidence available. For example, the computer-implemented product may generate a plurality of metadata tags and metadata tables that identify an estimated level of evidence for different sources. The computer-implemented product may also capture and store in the database prior searches, to generate a record of potential emerging associations between medications and adverse health outcomes.

Yet another aspect of the present disclosure is directed to a system that may record any actions taken on medications that are identified as possible causes of adverse health states. In such embodiments, the system may store information on whether medications were modified and whether health improvements were observed. In such embodiments, users may be available to report observations of medication related adverse health outcomes to regulatory authorities via standard mechanisms. For example, the system may collect forms such as Medwatch FDA form 3500. The system may also create a data repository that stores user information along with the saved searches from healthcare providers. The data repository may create an additional proprietary database for use by healthcare systems, the pharmaceutical industry, or insurance companies.

Another aspect of the present disclosure is directed to a computer-implemented method with the ability to extract and import EMR/EHR data, to permit searches for adverse health states that may be associated with medications, for specific individuals as well as for complete healthcare systems. The computer-implemented method may collect additional real-world data sources (for example insurance claim data) and explore the association between medications and adverse health states that are either unrecognized, or provide additional support for known associations to strengthen such linkages.

BRIEF DESCRIPTION OF THE DRAWINGS

The accompanying drawings, which are incorporated in and constitute a part of this specification, illustrate disclosed embodiments and, together with the description, serve to explain the disclosed embodiments. In the drawings:

FIG. 19 is an exemplary graphical user interface for search query input, in accordance with disclosed embodiments.

FIG. 21 is an exemplary graphical user interface for feedback input, in accordance with disclosed embodiments.

DETAILED DESCRIPTION

Figure 1:
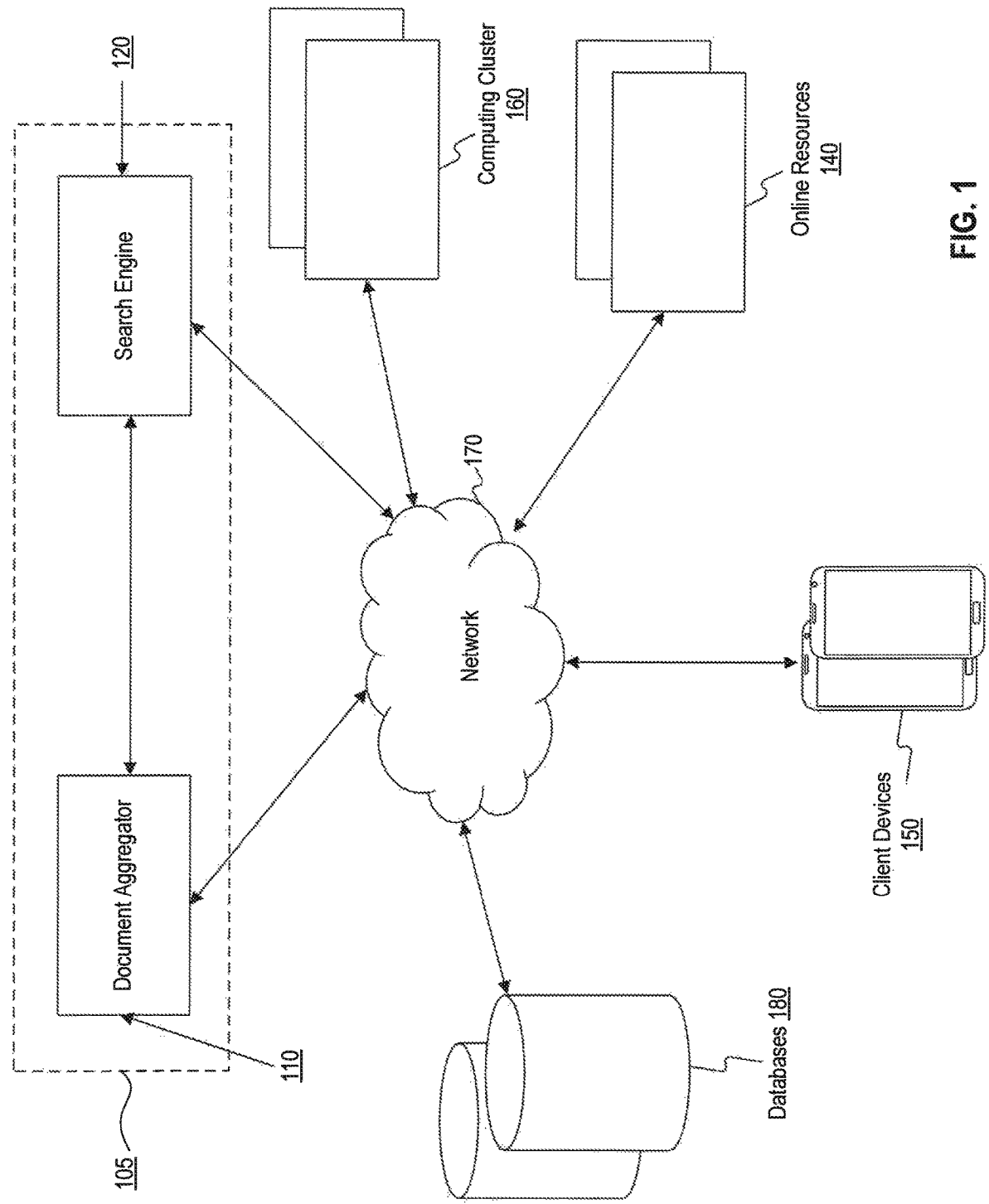
FIG. 1 is a block diagram of an exemplary system, in accordance with disclosed embodiments.

The disclosure is generally directed to a computer-implemented system that creates a data environment in which algorithms and artificial intelligence provide means to identify medication effects on disparate data sources/repositories/databases. Identifying medication effects may include locating, finding, or pinpointing records that report medication secondary effects. For example, identifying medication effects may include finding reports or literature of medication secondary effects. Alternatively, or additionally, identifying medication effects may include discovering or detecting secondary medication effects based on correlations identified by the computer-implemented system. For example, identifying medication effects may include performing statistical and machine learning methods to identify previously unrecognized or unreported correlations between, for example, symptoms and medications.

In some embodiments, the disclosed computer-implemented systems may rapidly extract relevant information from existing literature and databases, to generate synthesized, organized, and ranked abstracted information/evidence in a format that is pertinent to identify, reveal, or detect risks. For example, the computer-implemented system may extract machine readable content from existing literature, generate searchable markup language files, and associate literature with categorization metadata to provide information about medication secondary effects. Further, the disclosed computer-implemented system may use extracted information from the literature to inform and support decisions by correlating data and allowing users to efficiently locate relevant information of secondary effects. For example, in the disclosed systems and methods disparate information categories may be integrated into databases that are searched using industry or issue specific approaches to guide assessments and/or treatment. In some embodiments, the disclosed systems and methods may include creating databases for each industry. In such embodiments, based on the relevance for different industries, new associations are stored (previously unknown relationships between events and outcomes are uncovered) or existing associations are strengthened based upon user feedback which is added to each database.

In some embodiments, the disclosed systems and methods may enable post-trial secondary effects monitoring of medications to statistically identify potential secondary effects. Moreover, the disclosed systems and methods that may provide guided assessments and help researchers to narrow the possible causes of adverse health states and their relationship with medications. For example, in some embodiments the disclosed systems may collect, synthesize, and aggregate disparate data sources (such as medical literature and healthcare data sources) to identify correlations between adverse health effects and a medication. Moreover, the disclosed systems may create a secure proprietary repository of information, which can then be searched for health state/medication associations. In such embodiments, the repository may facilitate researchers to comply with Health Insurance Portability and Accountability Act of 1996 (HIPPA) regulations, while allowing researchers to easily manipulate and work with data searching correlations.

Moreover, the disclosed systems and methods may provide user interfaces that are accessible to a variety of users, including healthcare providers, healthcare systems, the insurance industry, the pharmaceutical industry, and any group undertaking large human healthcare investigations. For example, the disclosed systems and methods may employ intuitive graphical user interfaces to interact with users. With such configurations, the disclosed systems and methods may facilitate user adoption of the service, which may increase the number of users in the system and the amount of collected data used to discover correlations and secondary effects.

Further, the disclosed systems may leverage machine learning and data processing techniques to identify adverse health states caused by, or associated with, medications. For example, disclosed computerized methods may also allow users to identify trends and collect emergent relationships by aggregating and normalizing user input. Because the disclosed systems may expedite discovery of medications secondary effects, the disclosed systems may improve healthcare practice, enhance patient outcome, reduce healthcare system risks, and take significant unnecessary costs out of the medical system.

In certain embodiments, elements for the computer-implemented-system may include a processor configured to perform operations for determining relationships between medications and adverse effects. For example, processors in the disclosed systems may perform operations including: collecting records from multiple and diverse public databases and data sources; extracting, from existing data sources, relevant information associated with secondary effects; synthesizing databases to explore emerging trends evaluating factors (such as risk factors) and outcomes (both negative and positive); determining the evidence for relationships between signal and the events (e.g., "signal" may be the medication and "events" may be the symptom/disorder); acting on the relationship revealed from the synthesized and artificial intelligence results; creating new associations and strengthening existing associations between risk factors and outcomes through user feedback.

In some embodiments, the disclosed systems may be configured to identify emerging data trends from disparate data sources. With this information, the computer-implemented system may create causation links between inputs and events across health and safety surveillance situations. For example, based on user inputs searching a database, the disclosed systems may determine the relationship between a variable and an outcome.

In some embodiments, the disclosed systems may be tailored for specific industries. For example, in some embodiments, the system may receive search terms and norms, such as the acceptable rate of occurrence of risk events and the appropriate level of severity to merit detection/attention for health and safety concerns. As long as there is public information and sources that are difficult for practitioners to access (i.e., search and synthesize the information), the disclosed systems and methods may efficiently identify correlations. For example, the disclosed systems may be tailored to identify a product failure after it has been sold.

Some examples of industries include:
food industry (agriculture, chemical, and animal husbandry)—ability to cross reference sources of inputs and chemicals (i.e., types of inputs as well as source location of inputs) into the food source to look for and capture contamination, and conversely, to identify the ideal situations (i.e., better feed and water) for higher yielding results;
industrial/manufactured products—ability to cross reference sources of inputs (parts and labor) into industry products to identify potential resources for failure or malfunction of certain products; and
veterinary industry—symptoms and medications; Healthcare (humans)—described below. In some embodiments, the computer-implemented system may identify factors or situations that are linked to or predictive of good outcomes, which be applied to a wide variety of industries, such as Financial investment services.

Moreover, the disclosed systems and methods may synthesize and rank the extracted information using the available databases. In some embodiments, the systems and methods may not evaluate the veracity of existing data or certify the accuracy of the accepted public databases, or the value of it. The disclosed system and methods, however, may intelligently identify, aggregate, and apply, proprietary search methods to industry-specific data sources to identify relationships between events and outcomes through showing (and also creating) evidence of relationships. Moreover, in certain embodiments, the disclosed systems and methods may also reveal a lack of high-level evidence and/or discover invalid, inaccurate, unsubstantiated, unsupported, or potentially false, records. For example, the disclosed systems and methods may identify medications that lack proper documentation, or compare records from different sources to identify ambiguous or corrupted records.

Reference will now be made in detail to the disclosed embodiments, examples of which are illustrated in the accompanying drawings.

FIG. 1 is a block diagram of an exemplary system 100, in accordance with disclosed embodiments. System 100 may be configured to identify correlations between adverse or secondary effects and medications based on data collected from a plurality of sources. System 100 may include an identification system 105 which may include document aggregator 110 and search engine 120. System 100 may additionally include online resources 140, client devices 150, computing cluster 160, and databases 180. In some embodiments, as shown in FIG. 1, each component of system 100 may be connected to a network 170. However, in other embodiments components of system 100 may be connected directly with each other, without network 170.

Online resources 140 may include one or more servers or storage services provided by an entity such as a provider of website hosting, networking, cloud, or backup services. In some embodiments, online resources 140 may be associated with hosting services or servers that store web pages of health care services with electronic health records or web pages with medication information. In other embodiments, online resources 140 may be associated with a cloud computing service such as Microsoft Azure™ or Amazon Web Services™. In yet other embodiments, online resources 140 may be associated with a messaging service, such as, for example, Apple Push Notification Service, Azure Mobile Services, or Google Cloud Messaging. In such embodiments, online resources 140 may handle the delivery of messages and notifications related to functions of the disclosed embodiments, such as image compression, notification of identified medication alerts, and/or completion messages and notifications.

Client devices 150 may include one or more computing devices configured to perform one or more operations consistent with disclosed embodiments. For example, client devices 150 may include a desktop computer, a laptop, a server, a mobile device (e.g., tablet, smart phone, etc.), a gaming device, a wearable computing device, or other type of computing device. Client devices 150 may include one or more processors configured to execute software instructions stored in memory, such as memory included in client devices 150. Client devices 150 may include software that when executed by a processor, performs Internet-related communication and content display processes. For instance, client devices 150 may execute browser software that generates and displays interfaces including content on a display device included in, or connected to, client devices 150. Client devices 150 may execute applications that allows client devices 150 to communicate with components over network 170, and generate and display content in interfaces via display devices included in client devices 150. The display devices may be configured to display graphical user interfaces described in connection with FIGS. 16-21. The disclosed embodiments are not limited to any particular configuration of client devices 150. For instance, a client device 150 may be a mobile device that stores and executes mobile applications that provide functions offered by identification system 105 and/or online resources 140, such as providing information about medications in a database 180. In certain embodiments, client devices 150 may be configured to execute software instructions relating to location services, such as GPS locations. For example, client devices 150 may be configured to determine a geographic location and provide location data and time stamp data corresponding to the location data. In yet other embodiments, client devices 150 may have camera 520 to capture video and/or images:

Computer cluster 160 may include a plurality of computing devices in communication. For example, in some embodiments, computer cluster 160 may be a group of processors in communication through fast local area networks. In other embodiments, computer cluster 160 may be an array of graphical processing units configured to work in parallel as a GPU cluster. In such embodiments, computer cluster may include heterogeneous or homogeneous hardware. In some embodiments, computer cluster 160 may include a GPU driver for each type of GPU present in each cluster node, a Clustering API (such as the Message Passing Interface, MPI), and VirtualCL (VCL) cluster platform such as a wrapper for OpenCL™, that allows most unmodified applications to transparently utilize multiple OpenCL devices in a cluster. In yet other embodiments, computer cluster 160 may operate with distcc, and MPICH, Linux Virtual Server, Linux-HA, or other director-based clusters that allow incoming requests for services to be distributed across multiple cluster nodes.

Databases 180 may include one or more computing devices configured with appropriate software to perform operations consistent with providing identification system 105, search engine 120, and document aggregator 110 with data associated with medication images, medication features, and stored information about medication sales like cost or condition. Databases 180 may include, for example, Oracle™ databases, Sybase™ databases, or other relational databases or non-relational databases, such as Hadoop™ sequence files, HBase™ or Cassandra™ Database(s) 180 may include computing components (e.g., database management system, database server, etc.) configured to receive and process requests for data stored in memory devices of the database(s) and to provide data from the database(s).

While databases 180 are shown separately, in some embodiments databases 180 may be included in or otherwise related to one or more of identification system 105, document aggregator 110, search engine 120, and online resources 140.

Databases 180 may be configured to collect and/or maintain the data associated with patient complaints and taken prescription medication, and provide it to the identification system 105, search engine 120, and client devices 150. Databases 180 may collect the data from a variety of sources, including, for instance, online resources 140. Databases 180 are further described below in connection with FIG. 4.

Search engine 120 may include one or more computing systems configured to search databases. Search engine 120 may receive or obtain information from databases 180, computer cluster 160, and online resources 140. For example, search engine 120 may receive a plurality of images from databases 180 and online resources 140. Search engine 120 may also receive data from client devices 150.

In some embodiments, search engine 120 may receive requests from document aggregator 110. As a response to the request, search engine 120 may execute searches in a database to collect relevant information to aggregate.

In some embodiments, search engine 120 may use machine learning methods and develop functions to correlate information, such as a convolutional neural network or a Random Forest. Convolution neural networks may include a plurality of nodes. Each node may be associated with an activation function and each node may be connected with other nodes via synapses that are assoiled with a weight. The neural networks may model input/output relationships of variables and parameters by generating a number of interconnected nodes which contain an activation function. The activation function of a node may define a resulting output of that node given an argument or a set of arguments.

Artificial neural networks may generate patterns to the network via an "input layer," which communicates to one or more "hidden layers" where the system determines regressions via weighted connections. Search engine 120 may also utilize Random Forests, composed of a combination of decision tree predictors. (Decision trees may include a data structure mapping observations about something, in the "branch" of the tree, to conclusions about that thing's target value, in the "leaves" of the tree.) Each tree may depend on the values of a random vector sampled independently and with the same distribution for trees in the forest. Identification models may additionally or alternatively include classification and regression trees, or other types of models known to those skilled in the art. Search engine 120 may submit models to identify a medication. To generate identification models, search engine 120 may analyze data stored in database 180. Search engine 120 is further described below in connection with FIG. 3.

Document aggregator 110 may include one or more computing systems configured to perform one or more operations consistent with collecting, normalizing, and analyzing data to identify correlations between complaints and medications. In some embodiments, document aggregator 110 may receive complaints from client devices 150, correlate users with a health record using database 180, and establish relationships between medications and complaints. In some embodiments, document aggregator may also use machine learning techniques, previously disclosed.

FIG. 1 shows document aggregator 110 and search engine 120 as different components. However, document aggregator 110 and search engine 120 may be implemented in the same computing system. For example, elements in identification system 105 may be embodied in a single server.

Network 170 may be any type of network configured to provide communications between components of system 100. For example, network 170 may be any type of network (including infrastructure) that provides communications, exchanges information, and/or facilitates the exchange of information, such as the Internet, a Local Area Network, near field communication (NFC), optical code scanner, or other suitable connection(s) that enables the sending and receiving of information between the components of system 100. In other embodiments, one or more components of system 100 may communicate directly through a dedicated communication link(s).

It is to be understood that the configuration and boundaries of the functional building blocks of system 100 have been defined herein for the convenience of the description. Alternative boundaries can be defined so long as the specified functions and relationships thereof are appropriately performed. Alternatives (including equivalents, extensions, variations, deviations, etc., of those described herein) may be apparent to persons skilled in the relevant art(s) based on the teachings contained herein. Such alternatives fall within the scope and spirit of the disclosed embodiments.

Figure 2:
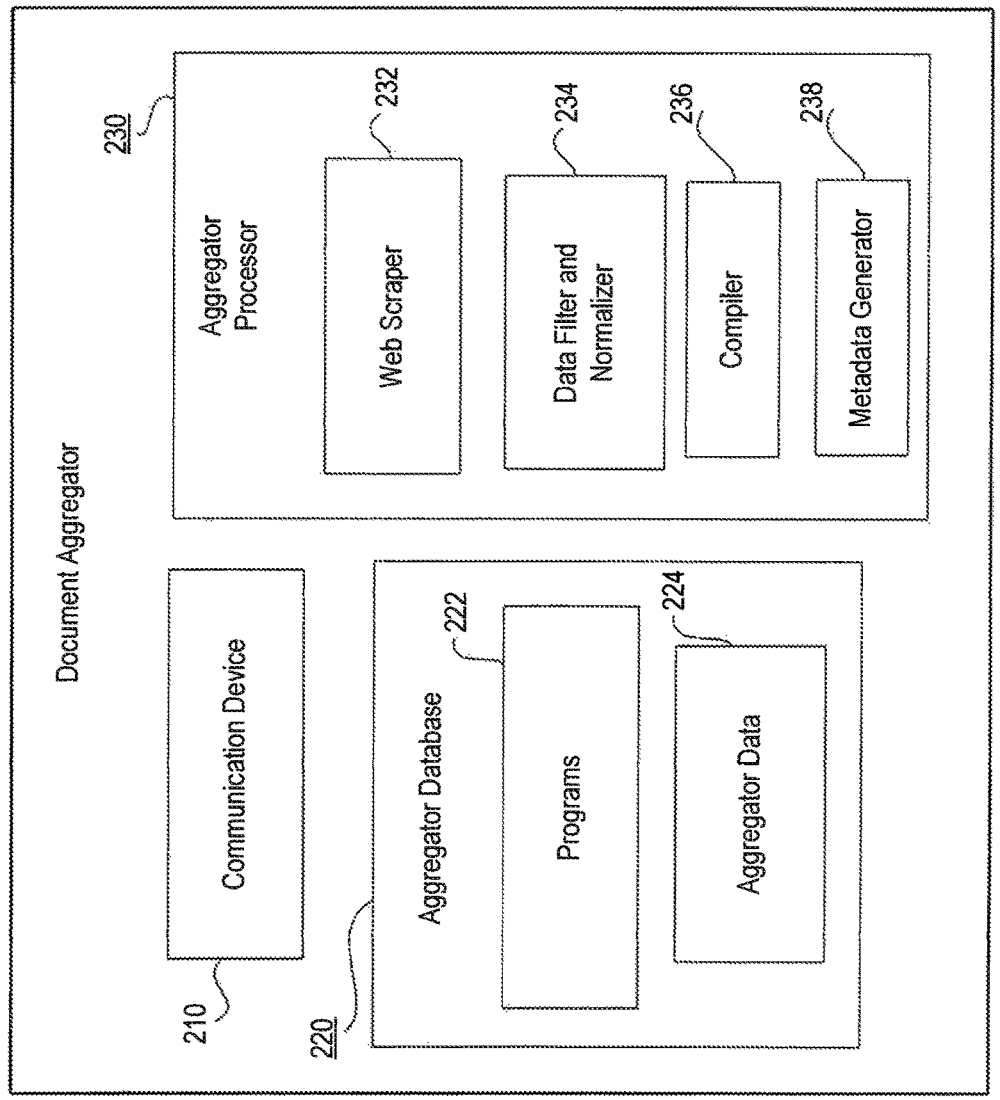
FIG. 2 is a block diagram of an exemplary document aggregator, in accordance with disclosed embodiments.

FIG. 2 is a block diagram of an exemplary document aggregator 110, in accordance with disclosed embodiments. Document aggregator 110 may include a communication device 210, an aggregator database 220, and one or more aggregator processors 230. Aggregator database 220 may include programs 222 and aggregator data 224. Aggregator processor 230 may include web scraper 232, data filter and normalizer 234, compiler 236, and metadata generator 238.

In some embodiments, document aggregator 110 may take the form of a server, general purpose computer, mainframe computer, or any combination of these components. In other embodiments, document aggregator 110 may be a virtual machine. Other implementations consistent with disclosed embodiments are possible as well.

Communication device 210 may be configured to communicate with one or more databases, such as databases 180 described above. In particular, communication device 210 may be configured to receive search results from search engine 120 for client device 150 queries. In addition, communication device 210 may be configured to communicate with other components as well, including, for example, online resources 140.

Communication device 210 may include, for example, one or more digital and/or analog devices that allow communication device 210 to communicate with and/or detect other components, such as a network controller and/or wireless adaptor for communicating over the Internet. Other implementations consistent with disclosed embodiments are possible as well.

Aggregator database 220 may include one or more storage devices configured to store instructions used by aggregator processor 230 to perform functions related to disclosed embodiments. For example, aggregator database 220 may store software instructions, such as program 222, that may perform one or more operations when executed by aggregator processor 230. The disclosed embodiments are not limited to separate programs or computers configured to perform dedicated tasks. For example, aggregator database 220 may include a single program 222 that performs the functions of document aggregator 110, or program 222 may include multiple programs. Aggregator database 220 may also store aggregator data 224 that is used by program(s) 222.

In certain embodiments, aggregator database 220 may store sets of instructions for carrying out processes to correlate medications with complaints, described below in connection with FIGS. 7-8.

In some embodiments, aggregator processor 230 may include one or more known processing devices, such as, but not limited to, microprocessors from the Pentium™ or Xeon™ family manufactured by Intel™, the Turion™ family manufactured by AMD™, or any of various processors from other manufacturers. However, in other embodiments, aggregator processor 230 may be a plurality of devices coupled and configured to perform functions in accordance with the disclosure.

Aggregator processor 230 may include a web scraper 232, a data filter and normalizer 234, a compiler 236, and a metadata generator 238. In some embodiments, aggregator processor 230 may execute software to perform functions associated with each component of aggregator processor 230. In other embodiments, each component of aggregator processor 230 may be an independent device. In such embodiments, each component may be hardware configured to specifically process data. For example, web scraper 232 may be a field-programmable gate array (FPGA), data filter and normalizer 234 may be a Graphics processing unit (GPU), and compiler 236 may be a central processing unit (CPU). Other hardware combinations are also possible. In yet other embodiments, combinations of hardware and software may be used to implement aggregator processor 230.

In some embodiments, aggregator processor 230 may aggregate and map the data from data acquisition sources based on classification outlines and store them in a aggregator database 220. In such embodiments, aggregator database 220 may be implemented as a Hadoop™ data storage. Further, Elasticsearch, or similar open source engines, may be employed to index and map the aggregated data. With this configuration, aggregator processor 230 may organize medication adverse events by system, organ, class, and/or preferred term (PT) and maintain these searches in the database.

Web scraper 232 may collect data from websites—like PDF documents or online medical forms. In some embodiments, aggregator processor 230 may implement web scraper 232 by executing instructions to create an application in which images are received and transformed. In other embodiments, however, web scraper 232 may be a separate device or group of devices.

In some embodiments, web scraper 232 may be configured for specific databases or sources. For example, web scraper 232 may be configured to collect records from specific databases containing medication literature (e.g., Drugs@FDA). Further, web scraper 232 may be configured to collect FDA warnings for Class I or II recalls for medications and may be configured to gather information from labeling collections submitted to the FDA. For example, web scraper 232 may collect FDA "Warning Letters." Thus, web scraper may be configured to collect product information and indications for use, dosage form, route of administration, and the recommended dosage. In such embodiments, web scraper 232 may implement a series of rules to extract information from the specific database. The rules may apply to websites, documents, and/or medical forms and may include matching basic key terms to identify articles that associate secondary effects with medications. For example, web scraper 232 may extract machine readable content from articles in databases, identify a list of terms, and determine if the article is associated with secondary or adverse effects. The list of terms may include: "safety," "complication(s)," "deficit," "deficiency," "hypo," "hyper," "adverse effect," "adverse event," "adverse events (AEs)," "side effect," "toxicity," "poisoning," "severe adverse event (SAE)," "TEAE (treatment emergent adverse event)," "treatment-emergent AE/SAE," "DLT (dose limiting toxicity)," "MTD (maximum tolerated dose)," "combination therapy (flagged)," "lab Abnormality/abnormalities," "laboratory abnormality/abnormalities," "laboratory complexities," "electrocardiogram (ECG)/electrocardiogram (EKG)—abnormality/abnormalities," "imaging—abnormality/abnormalities," "electroencephalogram (EEG)—abnormality/abnormalities," "magnetic resonance imaging (MRI)—abnormality/abnormalities," "ultrasound—abnormality/abnormalities," "radiograph—abnormality/abnormalities," "computed tomography (CT) scan—abnormality/abnormalities," "X-ray—abnormality/abnormalities," "electroretinography (ERG)—abnormality/abnormalities," "visual evoked potential (VEP)—abnormality/abnormalities," "electromyography (EMG)—abnormality/abnormalities," "nerve conduction velocity (NCV)—abnormality/abnormalities," "pulmonary function—abnormality/abnormalities," and/or "doppler—abnormality/abnormalities."

Rules for web scraper 232, or similar tools to retrieve information from databases 180 or online resources 140, may also employ term modifiers such as "associated with," "related to," "caused by," "induced by," "correlated with," and/or "most common/commonly reported." Moreover, the rules for content extraction may include ignoring—or not including—articles that: lack human data; include only animal or experimental animal data only; relate to species anything other than human or man or woman; or other animals. Further, the rules for content extraction may also include searching medication or drug labels.

In some embodiments, after aggregator processor 230 identifies articles, aggregator processor 230 may perform operations to capture specific information from articles. For example, after web scraper 232 identifies relevant records, aggregator processor 230 may extract machine readable content, using tools such as optical character recognition, to pinpoint information relevant to secondary or adverse effects. Further, web scraper 232, or other element of aggregator processor 230, may capture tables containing causes of problems using the specific keywords. The captured tables may be sectioned using Adverse Events (AEs), Severe Adverse Events (SAEs), complications, and/or secondary effects related to medications and capture a percentage (such as <=1% or >=1%) to identify medical problems that are related to the medication. In some embodiments aggregator processor 230 may be configured to capture less frequent but high impact adverse events. For example, aggregator processor 230 may capture events that led to death, medication discontinuation, study termination, or serious adverse events (SAEs).

The identification of relevant content may be guided by specific sections of articles or records. For example, aggregator processor 230 may assess relevance of documents by capturing abstract, methods, or keywords sections of the article to evaluate its relevance. Additionally, information in these sections may be used to determine a Level of Evidence (LoE) that is then used by metadata generator 238 to organize results and tables from articles. For example, the information in abstract sections may be used to classify records in Class I to Class IV LoE based on the matching key words from the definitions for LoE as further described below. In these embodiments, aggregator processor 230 may also apply specific rules for capturing information. For example, aggregator processor 230 may employ rules to specifically capture tables containing causes and problems by identifying keywords.

Alternatively, or additionally, aggregator processor 230 may invoke application programming interfaces (APIs) to retrieve records from the multiple databases including medication records. For example, web scraper 232 may be configured to invoke an API for FDA Adverse Event Reporting System (FAERS) Public Dashboard and retrieve multiple records with a single query. In such embodiments, aggregator processor 230 may be configured to download healthcare provider searches, FAERS summary tables/histograms for the actual number of patients with each problem, and summaries of reports.

Aggregation operations from aggregator processor 230 may be configured to be periodic. For example, aggregator processor 230 may be configured to retrieve records on a quarterly basis. Alternatively, aggregator processor 230 may perform updates monthly. In some embodiments, the update frequency of aggregator processor 230 may be based on the update frequency of the target resource. For example, Drugs@FDA may be updated daily but other databases, such as PubMed, may be updated weekly.

In some embodiments, aggregator processor 230 may perform capturing functions with data filter and normalizer 234. For example, data filter and normalizer 234 may be configured to extract features from a received document and create new files with normalized features. In such embodiments, data filter and normalizer 234 may use deep learning models such as Fast R-CNN can be used for automatic feature extraction. In yet other embodiments, Histogram of Oriented Gradients (HOG), Speeded-Up Robust Features (SURF), Local Binary Patterns (LBP), Color histogram, and Haar wavelets may also be used to extract features from a received image.

Aggregator processor 230 may implement data filter and normalizer 234 by executing software to create an environment for extracting image features. However, in other embodiments, data filter and normalizer 234 may include independent hardware with specific architectures to improve the efficiency of aggregation or sorting processes. For example, data filter and normalizer 234 may be a GPU array configured to partition and analyze layers in parallel. Alternatively, or additionally, data filter and normalizer 234 may be configured to implement a programming interface, such as Apache Spark, and execute data structures, cluster managers, and/or distributed storage systems. For example, data filter and normalizer 234 may include a resilient distributed dataset that is manipulated with a standalone software framework and/or a distributed file system.

In some embodiments, data filter and normalizer 234 may be configured to perform operations to extract machine readable content and generate searchable files. Data filter and normalizer 234 may extract content from records (including PDF, BMP, TIFF, JPEG, and PNG files), by first loading the files as image. Once the file is loaded, data filter and normalizer 234 may modify image quality and orientation by removing "noise" (a/k/a varying brightness or color) or straightening the image. Data filter and normalizer 234 may also remove lines that are in the full document to enhance quality of machine content extraction.

After processing the image, data filter and normalizer 234 may analyze the image to identify detection of text positions, white space, and the prioritization of important text areas or sections. For example, data filter and normalizer 234 may identify tables section to prioritize content extraction. Then, data filter and normalizer 234 may identify individual words and entire lines of data and fix "broken" or "merged" characters. Data filter and normalizer 234 may then recognize each character in the identified text to translate images to machine readable content. For example, records retrieved form the plurality of databases may be converted into a character code. Once machine readable content has been extracted from the records, data filter and normalizer 234 may save the extract content in a desired searchable format. For example, data filter and normalizer 234 may save the extracted content in XML files that may be used by compiler 236 to generate indexed files.

Compiler 236 may organize information retrieved from records and compile instructions to execute aggregation tasks. For example, compiler 236 may use a model from search engine 120 and apply inputs based on a request from client device 150. Moreover, compiler 236 may index files and generate database entries to facilitate query resolutions. For example, compiler 236 may structure machine readable content with different categories to improve search efficiency. In such embodiments, compiler 236 may categorize extracted information from the most serious/severe AEs to common AEs under the Safety/Toxicity section. Compiler 236 may also categorize records by Level of Evidence (LoE) and index them to allow for efficient search. Compiler 236 may also be configured to stored extracted information in a proprietary database and indexed for search.

In some embodiments, aggregator processor 230 may use metadata generator 238 to label records and/or extracted content to facilitate future searches or rank relevance of records. Metadata generator 238 may generate tags, such as HTML tags, that provide metadata about records, like a description or a LoE category. These meta tags may be used by search engine 120 to help index and to provide relevant content in their search results.

Metadata generator 238 may associate medication records with metadata tags, which may be stored (for example) in a database such as a MySQL database, using a metadata matrix. When a file is selected for tagging, metadata generator 238 may create a row for the file, in the metadata matrix. If the row already exists in the metadata matrix, and the file has been successfully tagged, then metadata generator 238 may release the record and not process the record. However, if the record has not being tagged, metadata generator 238 may generate metadata columns associated with a medical review file. For example, metadata generator 238 may generate columns in the metadata matrix of:

File ID—System generated,
Medication ID—Associated medication
File Name—This as shown in the origin server
File Path—Path to the file on the origin server.
File Create Date—The date this file was first processed
File Modified Date—Any updates to this file.
Reprocess File—If the file needs to be processed again
File Job Status—whether the record or file is in line for tagging
File OCR Status—Successfully Processed or not
OCR Process Error—Capture OCR exception message
File Apache Status—Successfully Processed or not (e.g., Tika™ status)
Apache Processing Error—Capture Apache exception message
File Index Status—Successfully Indexed (e.g., successful Solr™)
File Index Error—Capture indexing exception message.

In some embodiments, metadata generator 238 may be configured to tag records with a LoE. The level of evidence may be based on the source of the record (i.e., from which database it was retrieved) and/or keywords or combination of keywords present in the record. Metadata generator 238 may estimate the level of evidence and tag the record based on a class categorization. For example, metadata generator 238 may classify records retrieved by web scraper 232 in one of four categories: (1) first category may be for Masked (or blinded), randomized clinical trials, or meta-analyses of randomized clinical masked or blinded trials or controlled clinical trial. This category may be identified based on the source of the record such as records retrieved from Drugs@FDA, PubMed articles, (PubMed Central) PMC data classified, based on association with PubMed articles that are first category, and PMC data classified based on these keywords found in PMC articles; (2) second category may be for Unmasked or unblinded randomized clinical trial, open label trials, or uncontrolled studies (lacking one of these terms: controls, placebo, comparison group, comparative therapy), clinical trial phase 1. This category may include PMC data classified based on these keywords found in PMC articles; (3) a third category may include a cohort or case-control studies, observational study. This category may include PMC data classified based on these keywords found in PMC articles; (4) a fourth category of Case series, case reports, no controls, record or chart review, FAERS reports.

Categorization of records by metadata generator 238, or other elements of aggregator processor 230, may be based on the source of the record, a logical classification, or a combination of both. For the source based data classification, aggregator processor 230 may categorize medical review files data from Drugs@FDA as Class 1. Further, PubMed articles retrieved by running the query may also be classified as Class 1. In some embodiments, however, this classification may require validation, to determine if the query returns only Class 1 articles. Other sources, such as PMC articles associated with PubMed articles retrieved by running the query may also be classified as Class 1 but other sources, such as FAERS data, may be classified as Class 4.

To complement categorization based on source, aggregator processor 230 may classify data with a logic classified based on terms and/or combination of terms in the record. For this classification, aggregator processor 230 may evaluate each record performing the following steps. First, aggregator processor 230 may identify a "Methods" section. If "Method" section is not available, aggregator processor 230 may identify an "Abstract" section. Then, aggregator processor 230 may look for word combinations, of the classification criteria terms, in the "Method" or "Abstract" sections of the article. Based on terms aggregator processor 230 may classify each record. For example, if record includes terms of—masked+trial OR masked+clinical+trial OR randomized+clinical+trial OR blinded+clinical+trial, the record may be classified in class 1. If the record includes— Unmasked+clinical+trial OR unmasked+randomized clinical trial OR open+label+trials OR uncontrolled+studies OR clinical+trial+"phase 1" OR NOT(controls AND placebo AND comparison group AND comparative therapy), the record may be classified as class 2. Alternatively, or additionally, if the record includes—Cohort+studies OR case+control+studies OR observational OR study, it may be classified in class 3. Also if the record includes—case+series OR case+reports OR no+controls OR record+review OR chart+review OR FAERS+reports, the record may be classified in class 4. Further, if none of the above criteria are met, aggregator processor 230 may discard the record.

The components of document aggregator 110 may be implemented in hardware, software, or a combination of both, as may be apparent to those skilled in the art. For example, although one or more components of document aggregator 110 may be implemented as computer processing instructions embodied in computer software, all or a portion of the functionality of document aggregator 110 may be implemented in dedicated hardware. For instance, groups of GPUs and/or FPGAs may be used to quickly analyze data in aggregator processor 230.

Figure 3:
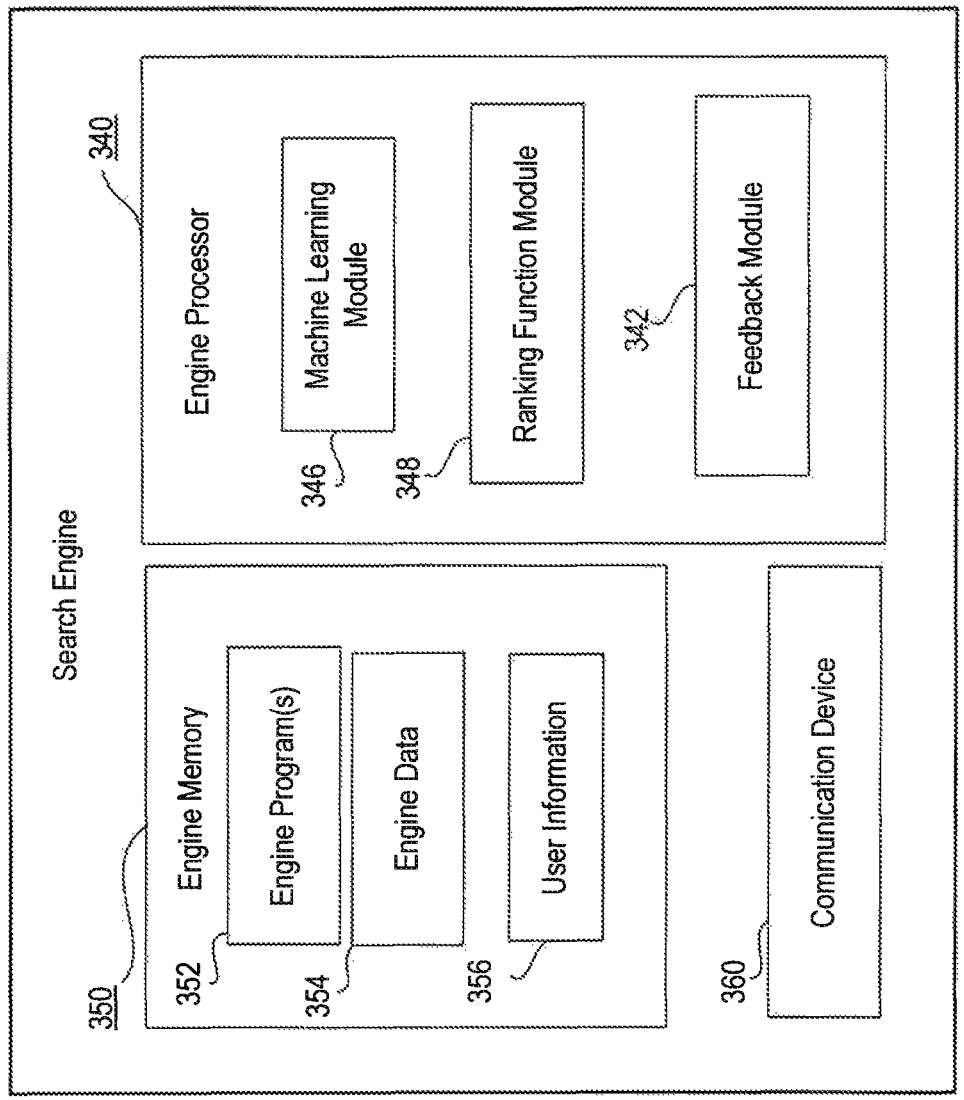
FIG. 3 is a block diagram of an exemplary search engine, in accordance with disclosed embodiments.

FIG. 3 is a block diagram of an exemplary search engine 120, in accordance with disclosed embodiments. Search engine 120 may include an engine processor 340, an engine memory 350, and a communication device 360.

In some embodiments, communication between search engine 120 and client devices 150 may happen over a secure connection. For example, communications between client devices 150 and identification system 105 may use secure sockets layer (SSL) protocols. In such embodiments, search engine 120 may perform identification and authentication functions. For example, search engine 120 may resolve concatenated passwords, that include added strings to the actual password. Then, search engine 120 may employ engine processor 340 to encrypt or decrypt hash functions. In such embodiments, engine memory 350 may include an authentication integrity validation. The program may be executed periodically and notify an administrator if there are any discrepancies in the results.

Alternatively, or additionally, access to search engine 120 may be protected with spring security. Spring security may include highly customizable authentication and access-control framework to provide a security framework that provides authentication and authorization support in order to Secure Spring-based applications. This may help with a comprehensive and extensible support for both Authentication and Authorization and may provide protection against attacks like session fixation, clickjacking, cross site request. Further, access to search engine 120 may utilize passwords that require a minimum size and complexity for the password. Complexity may require the use of minimum combinations of alphabetic, numeric, and/or non-alphanumeric characters in a user's password.

Alternative methods to grant access to identification system 105 and/or search engine 120 may be implemented. For example, search engine 120 may employ a Log 4j to support a logging process in terms of levels of priorities. In such embodiments, search engine 120 may offer mechanisms to direct logging information to a database and/or file and console. Search engine 120 may create a given Logger Object based on received user information, filter the information's it receives (for instance according to the severity of the alert), and forward logging data to a handler. Loggers may be assigned in different levels such as DEBUG, INFO, WARN and ERROR.

Alternatively, or additionally, search engine 120 may handle user session management to control access. Search engine 120 may perform an HTTP session related functionality and handle a combination of SessionManagementFilter and SessionAuthenticationStrategy interface. In such embodiments, search engine 120 may include programming for session-fixation protection attack prevention, detection of session timeouts, and restrictions on how many sessions an authenticated user may have open concurrently. Then, if a client device 150 is not currently authenticated, the filter may check whether an invalid session ID has been requested (because of a timeout, for example) and may redirect to the configured invalidSessionUrl if set.

Moreover, search engine 120 may control token based authentication to grant access of client devices 150. In such embodiments, a token may be employed for securing access to identification system 105. For example, search engine 120 may authenticate by ensuring that each request to a server is accompanied by a token, which the server verifies for authenticity and only then responds to the request. In some embodiments, every request may require the token to be sent in the HTTP header.

Engine processor 340 may include a processor similar to aggregator processor 230. Model processor may include a machine learning module 346, a ranking function module 348, and a feedback module 342. Machine learning module 346 may be software or hardware configured to create identification models based on training data. For example, machine learning module 346 may perform operations to generate predictive models or clustering algorithms or clustering techniques such as K-means clustering, mean-shift clustering, DBSCAN, or other similar techniques, as further described in connection with FIG. 15.

Ranking function module 348 may be software or hardware configured to assess the relevance of documents collected by document aggregator 110. In some embodiments, the level of evidence (LoE) of records identified during a search may not have been determined. For example, records retrieved during a search may not include metadata tags indicating the level of evidence. In such embodiments, engine processor 340 may determine the LoE once the record is identified for the search. Engine processor 340 may classify records in classes using techniques like the ones described for metadata generator 248 (FIG. FIG. 2). For example, engine processor 340 may using records' source and/or key terms to assign a classification to the record. In addition, ranking function module 348 may apply source based data classification and classify records based on whether they were retrieved from Drugs@FDA, PubMed, FAERS, among others. Alternatively, or additionally, ranking function module 348 may employ logic based data classification and determine a LoE for each record based on key terms and combinations of key terms in, for example, abstract, methods, and table sections. Further, in some embodiments, the LoE may be based in a table header describing type of evidence or experimentation.

Moreover, ranking function module 348 may be configured to assess the relevance of documents based on genetic information. For example, ranking function module 348 may determine relevance of records based on allele information received in a search query. In such embodiments, ranking function module 348 may be configured to process results of pharmacogenomic testing to identify relationships between secondary effects and specific genetic information. Based on genetic information, ranking function module 348 may determine the level of relevance of secondary effects, associating variants in one or more genes that can affect the response to certain medications.

Feedback module 342 may perform operations to receive and process feedback from users to expand the content of a proprietary database. In some embodiments, search engine 120 not only searches and presents information about secondary effects of medications, it may also collect additional information from physicians to be able to establish trends. In such embodiments, feedback module 342 may generate graphical user interfaces to receive user input. Further, feedback module 342 may process the feedback by generating an XML file for the feedback information and index it to facilitate future searches.

In some embodiments, feedback module 342 may be configured to retain the nature of searches requested, the user experience, and the generated search results. In such embodiments, feedback module 342 may include an acceptance criteria that would retain or discard feedback from client devices 150. For example, feedback module 342 may capture user feedback by retaining specific queries regarding medications and problems and creating a case number that the users may be able to use for future searches. Further, feedback module 342 may collect clinical user feedback via an automatic inquiry system, and/or tracking user ID. In such embodiments, feedback module 342 may capture two types of feedback. First, feedback module 342 may capture action feedback (action taken based on results of the search). Second, feedback module may capture outcome feedback (enter/update outcome) after action was taken, for the associated search query. With this configuration, queries submitted to search engine 120 may be used to enhance the collected information and identify trends of secondary effects for medications. Moreover, with this configuration feedback module 342 may provide information to aggregator processor 230 (FIG. 2) to train machine learning and artificial intelligence models and identify correlations between symptoms and medications.

In some embodiments, engine memory 350 may perform user authentication tasks. For example engine memory 350 may store user information 356 to determine the level of access of a user trying to authenticate to user search engine 120. For example, engine memory 350 may store user information 356 including Registered Email ID, Username, Enter Code, Password, Healthcare Network/Affiliation, Occupation, Specialty, Subspecialty, Years in Practice (post Graduate degree), and/or Contact number. Based on a predetermined level of access, an authenticating user may gain different access to search engine 120.

Figure 4:
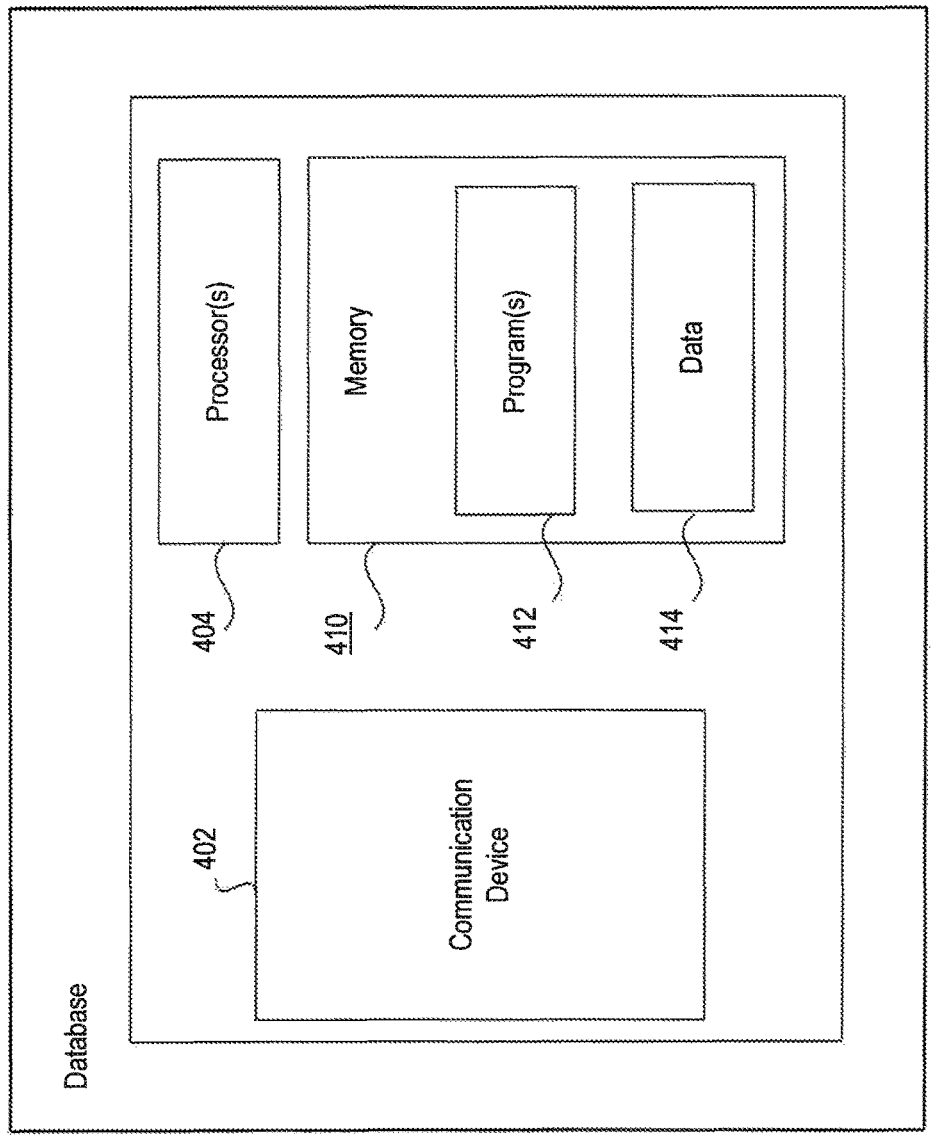
FIG. 4 is a block diagram of an exemplary database, in accordance with disclosed embodiments.

FIG. 4 is a block diagram of an exemplary database 180, in accordance with disclosed embodiments. Database 180 may include a communication device 402, one or more database processors 404, and database memory 410 including one or more database programs 412 and data 414.

In some embodiments, databases 180 may take the form of servers, general purpose computers, mainframe computers, or any combination of these components. Other implementations consistent with disclosed embodiments are possible as well.

Communication device 402 may be configured to communicate with one or more components of system 100, such as online resource 140, identification system 105, search engine 120, and/or client devices 150. In particular, communication device 402 may be configured to provide to search engine 120 documents and correlations between medication and complaints that may be used to generate a CNN or an identification model.

Database processors 404, database memory 410, database programs 412, and data 414, may take any of the forms described above for aggregator processors 230, aggregator database 220, programs 222, and aggregator data 224, respectively. The components of databases 180 may be implemented in hardware, software, or a combination of both hardware and software, as may be apparent to those skilled in the art. For example, although one or more components of databases 180 may be implemented as computer processing instruction modules, all or a portion of the functionality of databases 180 may be implemented instead in dedicated electronics hardware.

Data 414 may be data associated with electronic health care records or reports from FDA trials. For example, database 180 may include a renewable searchable database. In such embodiments, database 180 may be used to search by individual patient or patient's problems or symptoms against medications being utilized by the individual (currently, searches are conducted by medication to identify lists of problems). For example, database 180 may be used at the individual healthcare practitioner level and at the healthcare system level.

In some embodiments, database 180 may include an individual level seek function to a specific link between symptom and medication for an individual patient. In such embodiments, even if results show an overall low frequency event of a particular medication causing a condition, information is still relevant to keep causation in consideration when diagnosing root cause and treating an issue at the at the operative level.

Alternatively or additionally, database 180 may include a System level seek function. In such embodiments, database 180 may search for overall trends with particular illnesses and multiple medications. For example, a low frequency (# of occurrences) event can potentially be deprioritized in system level issues; however, if event, even a low frequency, causes a high severity outcome (i.e., death), presents risk to system which at the system level can be prioritized higher.

Database 180 may include new ways to organize existing databases, and create new databases from disparate data that did not interact/were connected previously. For example, database 180 may include a novel file type and data structure to weight the search results using criteria to rank the importance of the results (currently only review documents such as Cochrane reviews do this, and this is performed at a static time point).

Database 180 may additionally include system elements. System elements may describe speed of delivery when compared with current methods to obtain similar information (other searches would take hours or days and would not yield results as good). For example, in some embodiments database 180 may include information about the use of a frequently updated dynamic database created by synthesizing public domain publications/reports and FDA reports.

Further, database 180 may include software that search key terms (human, English, adverse effects of medications, complications of medications etc.) to create proprietary database. Database 180 may additionally perform searches at a speed of delivery needed for 'clinic' use for healthcare providers.

In some embodiments, database 180 may be implemented with open-source software and distributed computing. For example, database 180 may be implemented with Apache Hadoop™ software libraries to create a framework that allows for the distributed processing of large data sets. Further, database 180 may use indexing processes (e.g., Solr™) on a server to facilitate future searches. In such embodiments, databases 180 may perform operations of: setting environmental variables; running "gedit/etc/environment" command to open the environment file; editing path variable with following ":/usr/local/hadoop/sbin:/iusr/local/hadoop/binlhome/hadoop/Solr/bin," adding variables to the file and restart the system including JAVA_HOME, HADOOP_HOME, HADOOP_MAPRED_HOME, HADOOP_COMMON_HOME, and SOLR_HOME; copying solr.xml and zoo.cfg from SOLR_HOME/server/solr to SOLR_HOME; starting Hadoop™ using the following command "start-all.sh"; start Solr using "solr start -c;" and creating collection using following command "solr create -c." In some embodiments, with this routine database 180 may index information retrieve from records by aggregator processor 230 (FIG. 2) to facilitate future searches.

Moreover, databases 180 may include proprietary databases with cleaned and transformed medication information to utilize a defined list of terms and include both positive and negative associations that may guide the keywords for the search operations. In such embodiments, databases 180 may be configured to respond to queries using human language filters and tokens (plurals, tense, synonyms, stopwords); Proximity search, multi-value fields. Then, in such embodiments, databases 180 may allow client devices 150 to enter symptoms or findings for individual patient's problems and the current medications.

To facilitate queries in databases 180, databases 180 may be configured to associate patient symptoms and findings with 'auto-coded' MedDRA terms. Further, database 180 may include Hadoop to store data, relational database management system (RDBMS)/MySQL, and Elasticsearch to provide the infrastructure to host the data and APIs to, for example, search engine 120.

Figure 5:
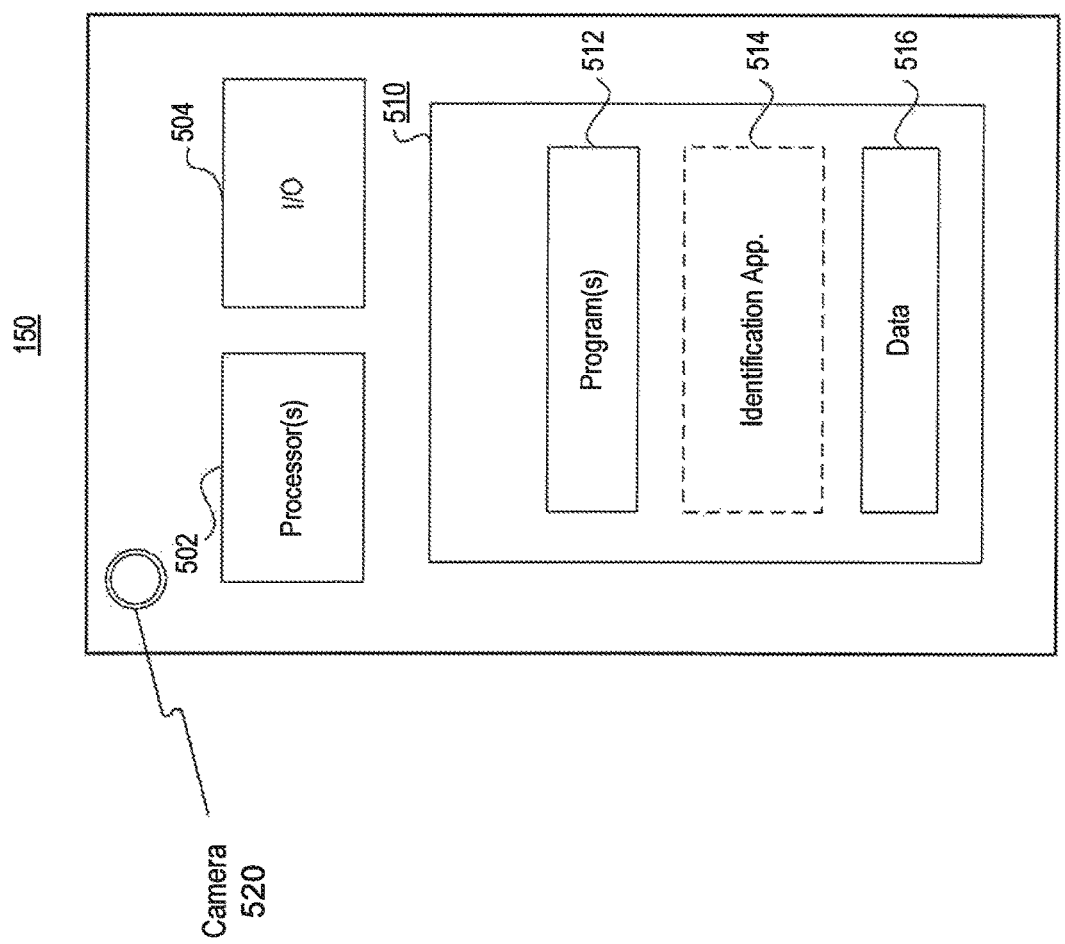
FIG. 5 is a block diagram of an exemplary client device, in accordance with disclosed embodiments.

FIG. 5 is a block diagram of an exemplary client device 150, in accordance with disclosed embodiments. In one embodiment, client devices 150 may include one or more processors 502, one or more input/output (I/O) devices 504, and one or more memories 510. In some embodiments, client devices 150 may take the form of mobile computing devices such as smartphones or tablets, general purpose computers, or any combination of these components. Alternatively, client devices 150 (or systems including client devices 150) may be configured as a particular apparatus, embedded system, dedicated circuit, and the like, based on the storage, execution, and/or implementation of the software instructions that perform one or more operations consistent with the disclosed embodiments. According to some embodiments, client devices 150 may include web browsers or similar computing devices that access web sites consistent with disclosed embodiments.

Processor 502 may include one or more known processing devices, such as mobile device microprocessors manufactured by Intel™, NVIDIA™, or various processors from other manufacturers. The disclosed embodiments are not limited to any specific type of processor configured in client devices 150.

Memory 510 may include one or more storage devices configured to store instructions used by processor 502 to perform functions related to disclosed embodiments. For example, memory 510 may be configured with one or more software instructions, such as programs 512 that may perform one or more operations when executed by processor 502. The disclosed embodiments are not limited to separate programs or computers configured to perform dedicated tasks. For example, memory 510 may include a single program 512 that performs the functions of the client devices 150, or program 512 may include multiple programs. Memory 510 may also store data 516.

In certain embodiments, memory 510 may store identification application 514 that may be executed by processor(s) 502 to perform one or more identification processes consistent with disclosed embodiments. In certain aspects, medication identification application 514, or another software component, may be configured to request identification from identification system 105 or determine the location of client devices 150.

I/O devices 504 may include one or more devices configured to allow data to be received and/or transmitted by client devices 150 and to allow client devices 150 to communicate with other machines and devices, such as other components of system 100. For example, I/O devices 504 may include a screen for displaying optical payment methods such as Quick Response Codes (QR), or providing information to the user. I/O devices 504 may also include components for NFC communication. I/O devices 504 may also include one or more digital and/or analog devices that allow a user to interact with client devices 150 such as a touch-sensitive area, buttons, or microphones. I/O devices 504 may also include one or more accelerometers to detect the orientation and inertia of client devices 150. I/O devices 504 may also include other components known in the art for interacting with identification system 105.

In some embodiments, client devices 150 may include camera 520 that is configured to take images or video and send it to other component of system 100 via, for example, network 170.

The components of client devices 150 may be implemented in hardware, software, or a combination of both hardware and software, as may be apparent to those skilled in the art.

Figure 6:
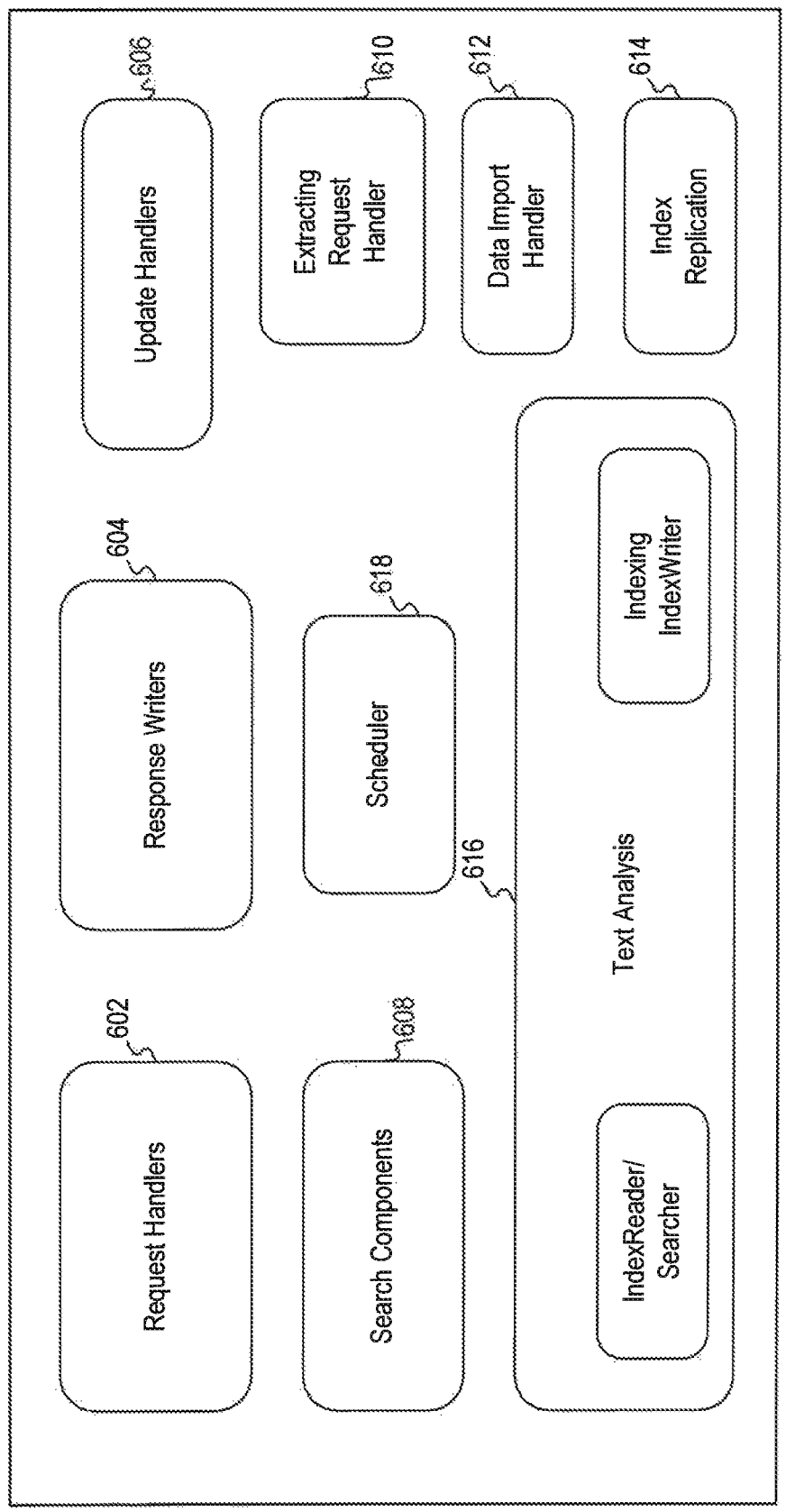
FIG. 6 is a block diagram of an exemplary identification system, in accordance with disclosed embodiments.

FIG. 6 is a block diagram of an exemplary identification system 105, in accordance with disclosed embodiments. As discussed in connection to FIG. 1, in some embodiments identification system 105 may include search engine 120 and document aggregator 110 in a single system. The embodiment shown in FIG. 6 shows an exemplary implementation of identification system 105 in a single component. In these embodiments, identification system 105 may apply a detection and analysis framework, written in Java, stewarded at the Apache Software Foundation. For example, identification system 105 may apply Apache Tika™ to detect and extract metadata and text from different file types. Further, in such embodiments, identification system 105 may apply a Java content detection framework to generate libraries with extracted content and employ command-line editions suitable for use from other programming languages.

As shown in FIG. 6, identification system 105 may include a series of handlers to process queries from client devices 150 including: request handlers 602, response writers 604, update handlers 606, search components 608, extracting request handler 610, data import handler 612. Further, identification system 105 may include an index replication 614, a text analysis module 616, and a scheduler 618.

Request handlers 602 may process a request to analyze records by sending it to an enterprise search platform such as Solr™. The requests may be index updates or search query. Further, based on the query, request handlers 602 may select a specific API that determines how the requests should be processed. Request handlers 602 may be mapped to the URI end-point which serves the request when a request is passed to the search platform.

Response writer 604 may format output for user queries. Response writer 604 may implement a writer in Apache Solr™ that writes response in formats such as XML, JSON, CSV, etc. Each type of response uses different response writers. The application may handle the output in JSON format. Update request handler 606 may be configured to re run requests through a set of plugins (signature, logging, indexing).

Search component 608 may perform spell checking, query, faceting, hit highlighting, etc. In some embodiments, search component 608 may be registered as search handlers. Further, multiple components may be registered with search component 608 to enable parallel searches. In some embodiments, search component 608 may parse queries using the search platform, like Solr™, to verify the query for syntactical errors and then translates them. For example, search component 608 may modify the search to Lucene understands.

Extracting request handler 610 may be configured to recognize data in the form of tokens. Extracting request handler 610 may divide content into tokens and pass these tokens to information retrieval software, such as Lucene. An analyzer may then examine the text of fields and generates a token stream. A tokenizer breaks the token stream prepared by the analyzer into tokens.

Data import handler 612 may read data residing in relational databases, build searchable documents by aggregating data from multiple columns and tables according to configuration, provide ability to do full imports according to configuration, and detect inserts/update deltas (changes) and do delta imports (we assume a last-modified timestamp column for this to work). Further, data import handler 612 may schedule full imports and delta imports, read and Index data from xml/(http/file) based on configuration, make it possible to plug in any kind of data-source (ftp, scp etc) and any other format of user choice (JSON, csv etc).

Index replication 614 may distribute complete copies of a master index to one or more slave servers. In some embodiments, index replication 614 may manage updates to a master index stored, for example, in databases 180. Index replication 614 may include a Java implementation of index replication that works over HTTP. The configuration of index replication 614 may be controlled by a single file (e.g., solrconfig.xml). Further index replication 614 may supports the replication of configuration files as well as index files, and use Java-based replication features.

Text analysis module 616 may be configured to analyze a text field and return tokens emitted by an analyzer in an array. Any analyzer chain that is attached to a field can be used with the analyze function. Text analysis module 616 may analyze chains of characters using chain analyzers and/or may define field types for content extractions. For example, text analysis module 616 may be configured to identify sections such as Abstract, Methods, and Tables. Text analysis module 616 may also perform term frequency-inverse document frequency (TF-IDF) to generate term vectors used to represent text documents when performing text mining and machine learning operations.

Scheduler 618 may be configured to schedule tasks or operations in identification system 105. For example, scheduler 618 may allow identification system 105 to track client devices 150 queries and create batched tasks or prioritize certain events. Scheduler 618 may also run a security program or updating software and may manage the job queue for handlers, such as response writers 604. Scheduler 618 may run at every fixed interval of time and invoke APIs to communicate with other elements of identification system 105.

Figure 7:
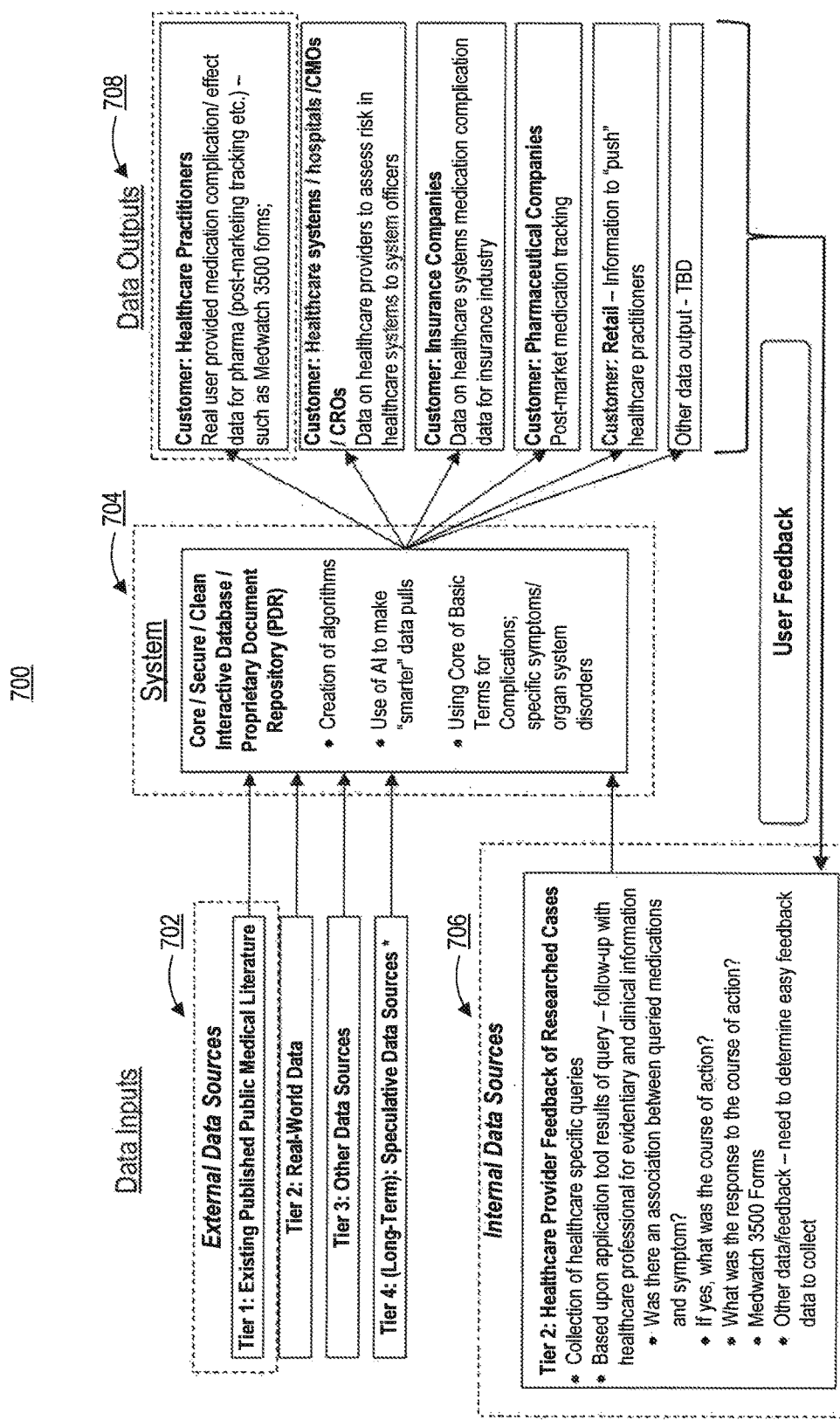
FIG. 7 is an exemplary flow chart illustrating a data collection and output process, in accordance with disclosed embodiments.

FIG. 7 is an exemplary flow chart illustrating a database construct process 700, in accordance with disclosed embodiments. In some embodiments, database construct process 700 may be executed by identification system 105.

Database construct process 700 may include data inputs, a system selection and data outputs. Data inputs may include external data sources 702 and internal data sources 706, further described in connection with figure FIG. 8.

External data sources 702 may be categorized in multiple tiers of data. For example, external data sources 702 may include a tier 1 of existing published public medical literature, a tier 2 of real-world data, a tier 3 of other data sources, and a tier 4 of speculative data sources. In such embodiments, tier 1 data may include information collected from academic or regulatory databases such as the National Library of Medicine or the Food and Drug Administration or other sources further described in connection to step 802 of FIG. 8. Alternatively or additionally, tier 4 data may include items collected with technology that provide ancillary data not immediately contributing to establish correlations but that may be used to train artificial intelligence algorithms. For instance, speculative data sources of tier 4 may include training data sets that are used to train convolutional neural networks to extract features that are not evident.

Moreover, in some embodiments, internal data sources 706 may include tier 2 health care provider feedback of research cases. In such embodiments, as further explained in connection to step 814, identification system 105 may collect queries from healthcare practitioners. Based on results of the query, identification system 105 may request following evidentiary support and a history of the patients record including, for example, a patient's response to treatment.

Database construct process 700 may also include system step 704 in which identification system 105 may clean data, create algorithms, and generate interactive databases. For example, as further described in connection to step 810 in FIG. 8, identification system 105 may normalize files or documents associated with medication complications. For instance, in step 704 identification system 105 may employ zonal optical character recognition to create text files from images that can be later used as inputs to artificial intelligence systems that determine correlations between medication complications and specific symptoms.

In data outputs step 708, identification system 105 may output information for customers or products. For example, identification system 105 may provide information to healthcare companies associated with medication complications using an Android or iOS application. In other embodiments, as further explained in connection to step 812 in FIG. 8, data outputs step 708 may include a desktop application that associates symptoms and disorders, specific medications, and a weighting value for the data. For example, in data outputs step 708 identification system 105 may generate and display listings of specific medications with a determined potential secondary effects.

Process 700 may create a Proprietary Document Repository (PDR) that may initially be created from existing published medical literature and FDA documents. Over time, additional documents could be added, as identified, that report associations between medications and secondary effects. The proprietary repository or core system may also have the capability to retain the results of searches (initiated by the healthcare providers) run with the product, and to capture user feedback (for example, response to stopping a medication) to be integrated into the PDR for future searches.

The process 700 may use contained, separate, and secured environment created from external sources. Data is more easily cleaned, managed and used for searches and machine learning for specific issues in a separate and secured company database. In addition, maintaining a separate and clean database from the sources may ensure protection of the product and continued functioning of the business even if external resources are corrupted.

In some embodiments, a core system may have an adaptive layer that pulls in more documents than needed to increase completeness and cleans specific documents to create the PDR. Relevant data may be extracted and cleaned prior to inclusion into secure environment. In addition, artificial intelligence (AI) capabilities can produce an adaptable system that learns and can accomplish more efficient data extraction and cleaning over time (using generic terms such as medication adverse effects, complications, toxicity; and more specific terms targeted to individual organ systems).

In some embodiments, a core system and PDR may reside in rented secure 'cloud' space via an existing commercial provider. For example, process 700 may use separate systems, one for external communications with users, industry, and business operations and one for the core data system to reduce the risk for virus/malware infection.

In some embodiments, a core system may be run in the background of hospital EMR/EHS and pharmacy EMS systems for every patient. For example, identification system 105 may capture primary complaints and medications via an adaptive layer that may take data in its existing form in order to run searches. Identification system 105 may proactively alert providers on possible known associations, may discover new possible associations for inclusion in future results and may collect additional information such as number of visits related to same compliant and medication.

In other embodiments, identification system 105 may capture from pharmacy manufacturer, version, and geography for point of origin for the medications from pharmaceutical systems for the purpose of tracking the safety and efficacy of specific medication batches, and possibly to alert providers if medication is ineffective or unsafe (potentially due to counterfeit or poor manufacturing).

In some embodiments, process 700 may result in database 180 storing information including Existing Published Public Medical Literature and FDA databases. Screening for inclusion in database may include. English only; Human subjects; Literature concerning clinical trials or other research involving medications (possibly using lists of key words from MedDRA database and WHO Drug Global dictionary: medications, pharmaceutical agent, medication therapy, individual medication names, secondary effects, complications, adverse effects, medication toxicity).

Identification system 105 may categorize literature, and then rank by class of evidence: Cochrane review, clinical trials (prospective study, randomized, etc.), masked or blinded studies, case series or reports.

In other embodiments, process 700 may include searches and captured data from healthcare provider users. Identification system 105 may search Electronic Medical Record (EMR) data/Electronic Health Record (EHS), Proposed method for inclusion in PDR and search results: Import medications for particular patient and large groups of patients from EMR system into the core system, tool needs to be built with ability to link into EMR and EHS systems (or receive de-identified data) to search for chief complaints, problem lists, symptoms and assessments in history and notes, and medications. In such embodiments, the compiled information may strengthen links between side-effect and medication with additional data in our core database.

In yet other embodiments, process 700 may result in database 180 including examination of additional real-world data sources that may further explore the association between medications and patient symptoms that can be used to further strengthen the linkages already reported in existing literature, or can be shown to illuminate associations that are currently unreported. For example, database 180 may include pharma companies with clinical trial data, Insurance companies with claims data. In other embodiments, during process 700 database 180 may include Speculative Data Sources to consider at later dates. For example, database 180 may include other data sources and analysis might include the following: Facial/image analysis; Hyperspectral analysis; Pharmacogenomics/genome sequencing; Radiology Information Systems/Diagnostic Imaging; Individual's Lab Data/Healthcare systems data/Epidemiology studies; and Information collected from sensors/wearable technology from individuals.

Figure 8:
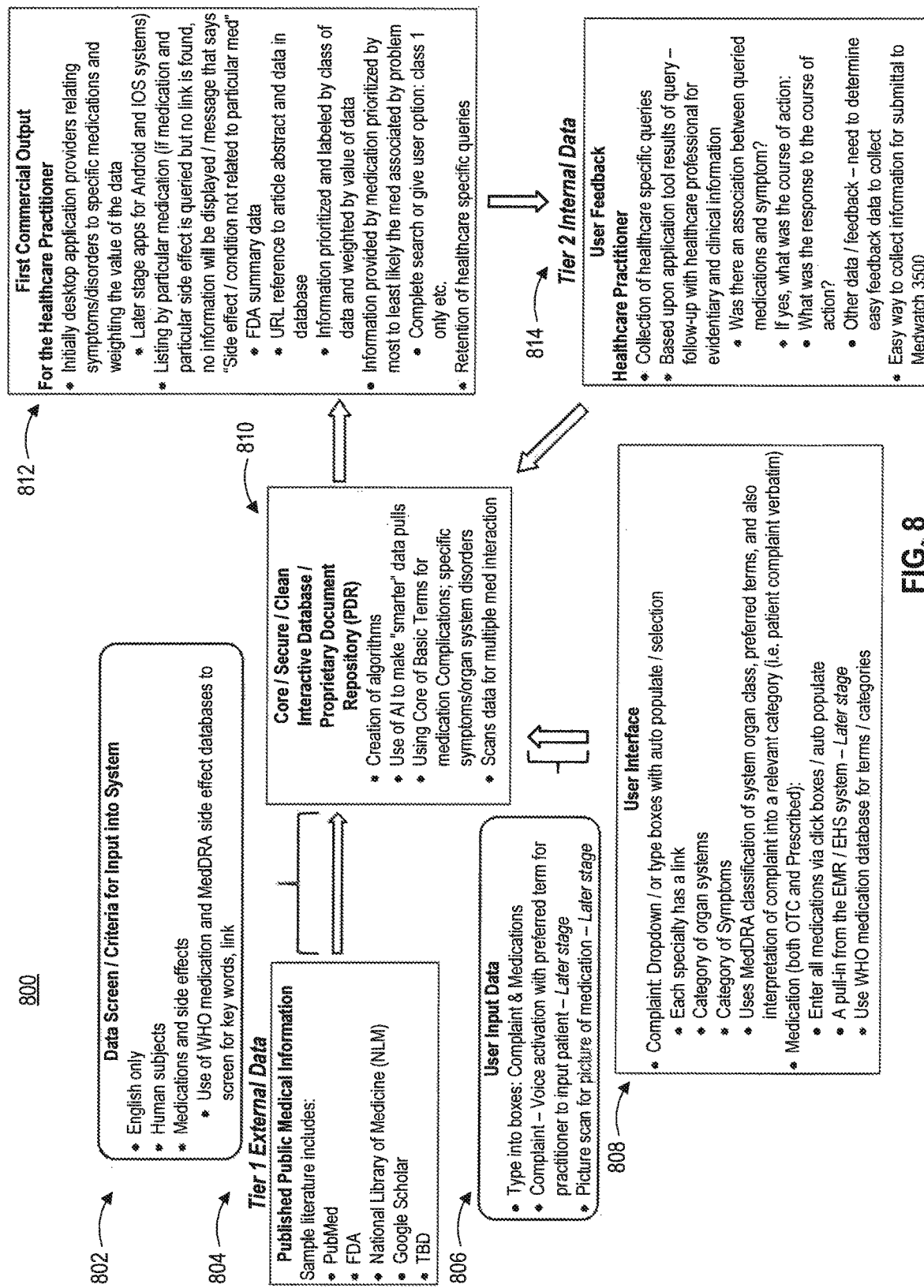
FIG. 8 is an exemplary flow chart illustrating a core system process, in accordance with disclosed embodiments.

FIG. 8 is an exemplary flow chart illustrating a core system process 800, in accordance with disclosed embodiments. In some embodiments, core system process 800 may be executed by identification system 105.

Identification system 105 may receive a data screen in step 802. Identification system may then query published public medical literature at step 804. In step 806, identification system 805 may receive user input by, for example, user inputs in a user interface in step 808.

In step 810, identification system 105 may use, for example, machine learning module 346 or data filter and normalizer 234 to develop algorithms for the correlation between medical complaints and prescribed medications.

Identification system 105 may then output first commercial information in step 812 and receive user feedback in step 814.

Identification system 105 may be primarily used by healthcare providers to deliver medical knowledge with the speed of delivery (i.e., within a few seconds) essential for the demands of clinical practice. The immediate output of identification system 105 may provide actionable information relevant to patient care management, based upon a unique search. Through efficient technology, the universe of relevant medical information may be screened and sorted into actionable medical knowledge to help guide the diagnostic reasoning and identification of patient treatment. At a later stage, identification system 105 may be usable for the pharmaceutical and insurance industries. However, in such applications comprehensiveness may be more important than speed for that market, as the information will not be needed for individual patient management. Alternatively, or additionally, identification system 105 may be intended for patients and families who do not have medical knowledge, where their searches may both be informative and 'drive' healthcare provider use of these products (i.e., a simplified version of the first core product).

In some embodiments, identification system 105 may list complaints and medications that may be utilized in a search that looks for text documents that contain both the complaint (s) and the medication(s). That search may be conducted on the Proprietary Document Repository (PDR) of text documents derived from the published literature and available documents from regulatory agencies in the United States and elsewhere, starting with, for example, the Food and Drug Administration (FDA).

In identification system 105, search inputs (Compliant and Medication) may be available on the screen for viewing with the output of the search process in order to easily facilitate changes to the search. In addition, The output of a search may be listed by each medication, and if no medication and complaint link is found, no information may be displayed, or a message will say that no association was found.

In some embodiments, the specific content of the output may include a reference (URL) to provide a link to the relevant FDA documents, existing published public medical literature article or abstract, or other documents in the PDR. In such embodiments, the URL may be listed by: Information prioritized and labelled by class (level of evidence) of data; Information provided by medication prioritized by most to least likely medication to be associated with the complaint.

In alternative embodiments, identification system 105 may only give evidence from randomized trials e.g., class 1 evidence only. A later version might be able to extract tables and graphs from the cited documents.

In certain embodiments, identification system 105 may retain both the nature of searches requested and the User impact of the product. This may be accomplished by following a process in which identification system may configure a processor to: retain specific queries regarding complaints and medications; collecting of clinical user feedback via an automatic inquiry system; collect feedback and track it by user ID, case number and date; based upon the results of the search; and offer a facile feedback system: For example, identification system 105 may determine whether the healthcare provider concluded there was an association between queried medications and complaint. If yes, identification system 105 may determine a course of action and a response to the course of action.

Figure 9:
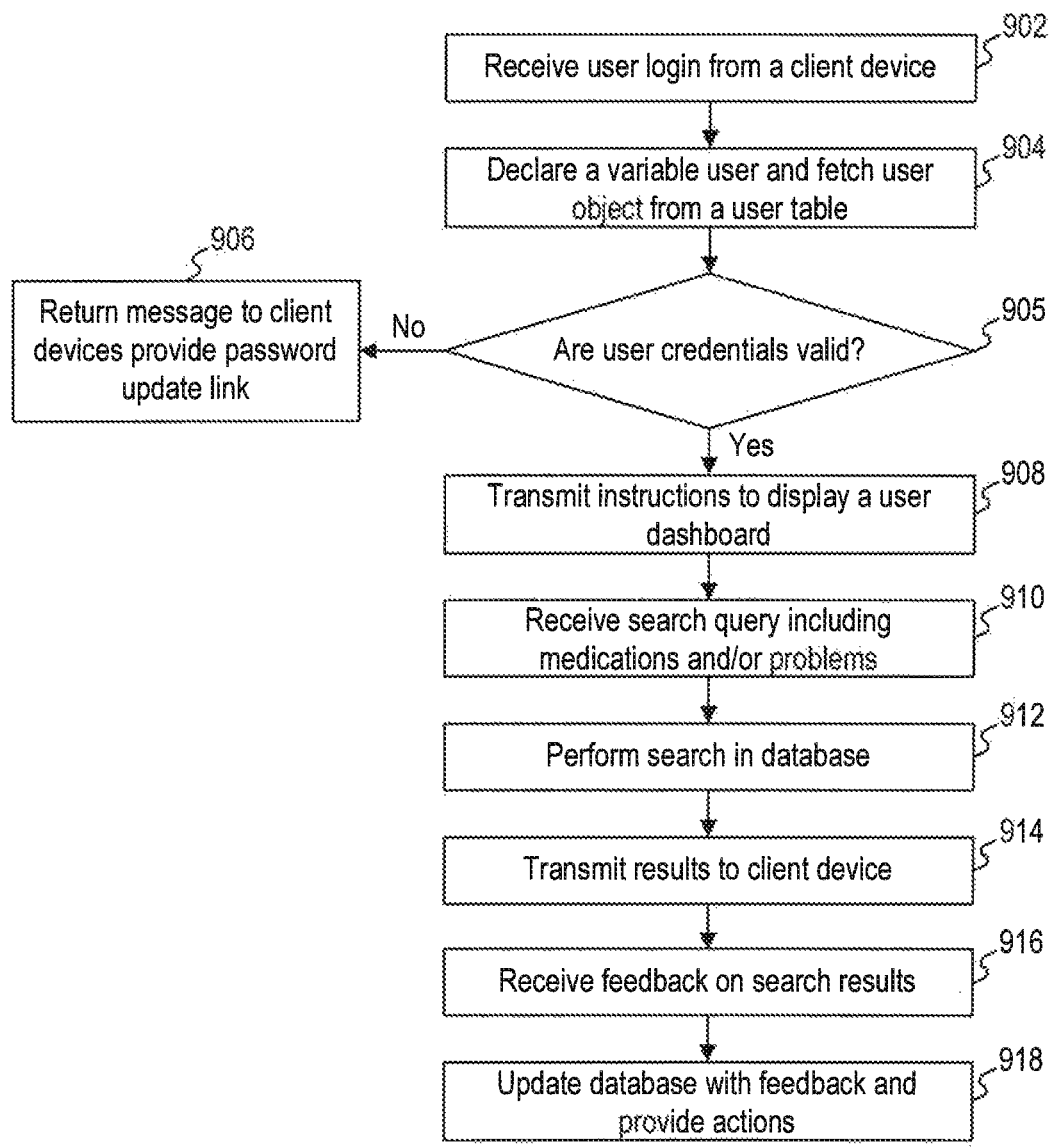
FIG. 9 is an exemplary flow chart illustrating an identification and feedback process, in accordance with disclosed embodiments.

FIG. 9 shows a flow chart illustrating an exemplary identification and feedback process 900, in accordance with disclosed embodiments. In some embodiments, process 900 may be carried out by identification system 105 (FIG. 1). In such embodiments, process 900 may be carried out by document aggregator 110 and/or search engine 120.

In step 902, identification system 105 may receive a user login from one of client devices 150. As further described in connection with FIG. 17, the login may include authentication information, such as user name and passwords. After receiving the login information, identification system 105 may declare a variable user and fetch a user object from a user table. For example, identification system may retrieve user information 356 from engine memory 350 (FIG. 3), to authenticate a user login.

In step 905, identification system 105 may determine whether the login includes valid credentials. For example, identification system 105 may compare the received credentials with user information 356 (FIG. 3). If the credentials are not valid (step 905: no), identification system 105 may continue to step 906 and return a message to client device 150 providing an error message and a link to update a password. However, if the credentials are valid (step 905: yes), identification system 105 may continue to step 908 and transmit instructions to display a user dashboard, as further described in connection with FIG. 18.

In step 910, identification system 105 may receive a search query from the authenticated client device 150. The search query may include one or more medications and a list of complications or symptoms. The query may specify medications by brand or generic names, and the symptoms may be coded with normalized terms. In step 912, identification system 105 may search for correlations between medications and symptoms in the index files generated by aggregator processor 230 or in databases 180. Results from the search, may be transmitted back the authenticated client device 150 in step 914.

Some secondary effects of medications are associated with the genetic characteristics of the patients. For instance, some medications may have different toxicity for specific genotypes. In some embodiments identification system 105 may use DNA and/or genetic information to narrow correlations between medications and symptoms. In some embodiments, the search query may include DNA information of a patient. For example, in addition to symptoms and medications, the search query received in step 910 may include genetic types and/or allele information. In some embodiments, identification system 105 may use the genetic information as a parameter to search for secondary effects and correlations, using, for example, search engine 120. Further in such embodiments, identification system 105 may use DNA to link potential secondary effects and provide markers to collect data and identify information.

The results transmitted in step 914 may include a summary followed by list of search results ranked by Classes of evidence (as Class 1 or Class II-IV that matches entered medication and problem), and medication recall Information. If the medication has been recalled, for example a warning for Class I or II recall has been issued for the medication, the results may output a prominent message at the end of search summary with toggle to show criteria for each of 3 categories (Class 1-3) but not displayed otherwise.

Results transmitted in step 914 may provide a link to recall information, if available. For example, when the medication in a search query from the authenticated client device 150 is associated with a Class I or II recall, results in step 914 may provide a link to a Warning Letter or the notice for Class I or II recall. Further, based on the medication and problem, identification system 105 may display records that contain both the query problems and medications. The results may include a display with medication and problem for viewing with the output of the search. Further, the results may display each medication associated with the problem. However, if no medication and problem link is found, the results may include a message indicating there was no association. The no association found between medication and problem may recite "These medications have not been reported to be associated with the listed clinical problem(s)."

In some embodiments, the specific content of the results in step 914 may include an extraction of the relevant table, reference (URL) to provide a link to the relevant FDA documents, existing published public medical literature article or abstract, or other documents in the PDR. For example, identification system 105 may transmit information to display links to downloaded medical review PDFs from Drugs@FDA, links to PubMed & PMC articles, links to FAERS public dashboard may be provided for the FAERS related data. Further, identification system 105 may transmit information to display links Drug Labels, such as Non-Steroidal Anti-Inflammatory Drugs (NSAID) labels and/or medication applications such as Blue Bird Labels.

In some embodiments, identification system 105 may use metadata tags, like the ones generated by metadata generator 238 (FIG. 2), to prioritize results based on LoE. Further, results transmitted in step 914 may be labelled by Class I and Class II-IV to provide users with a ranked classification of medications and potential associations from most to least likely medication to be associated with the problem.

Once the data is output, identification system 105 may receive feedback on the search results in step 916. This feedback may include evidentiary and clinical information that help establish whether there is a correlation between medications and symptoms. Further, the feedback received in step 916 may include an action by a healthcare practitioner and the resulting response to guide future assessments and provide guided diagnostics. Also, the feedback received in step 916 may be use as training or validation data to train machine learning algorithms.

In step 918, identification system 105 may update databases 180 and/or engine memory 350 to store the user feedback and include records for the potential association between medication and symptoms. With this configuration, identification system 105 may determine if there are trends of association between medications and symptoms.

Figure 10:
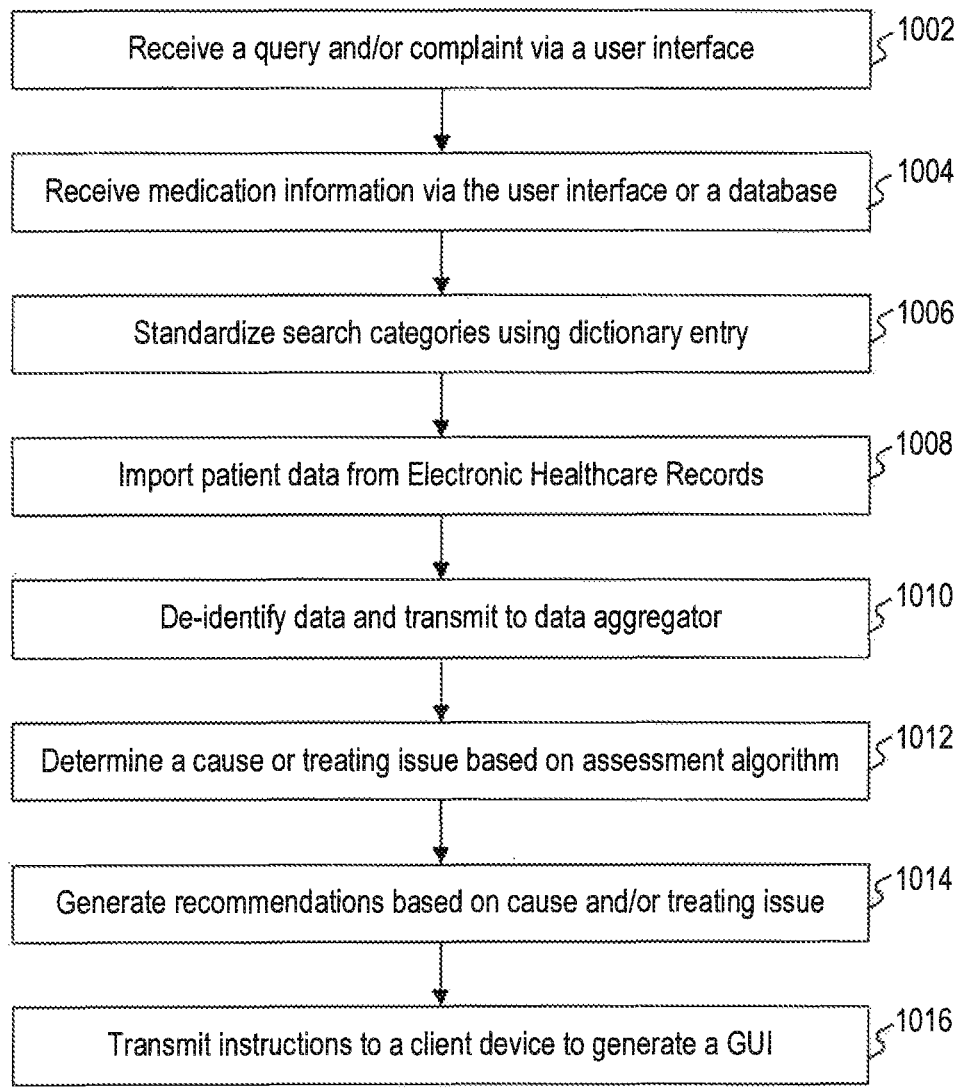
FIG. 10 is an exemplary flow chart illustrating a query request process, in accordance with disclosed embodiments.

FIG. 10 is an exemplary flow chart illustrating a query request process 1000, in accordance with disclosed embodiments. In some embodiments handling query request 1000 may be carried out by identification system 105.

In step 1002, identification system 105 may receive a query and/or complaint via a user interface. In some embodiments, the query and/or complaint may include DNA information that helps determine if a genotype is more prone to secondary effects or toxic reactions.

In step 1004, identification system 105 may receive medication information via a second graphical user interface, which may be different from the first user interface or a database. For example, identification system 105 may receive medication information and problems using drop-down menus as described in connection with the user interface shown in FIG. 19.

In step 1006, identification system 105 may standardize search categories using dictionary entries.

In step 1008, identification system 105 may import patient data from a database. For example, identification system 105 may import electronic healthcare records from an online resource 140. In such embodiments, importing electric healthcare records may include importing DNA information about a patient to help determine correlations between the medication and secondary effects. Because some secondary effects are tightly associated with specific genotypes, identification system 105 may import DNA information about patients in step 1008 to improve the accuracy of estimated correlations or causations.

In step 1010, identification system 105 may apply de-identification techniques before transmitting or aggregating data. For example, identification system 105 may apply algorithms to comply with HIPPA regulations.

In step 1012, identification system 105 may determine a correlation or causation for a complaint received. For example, using the information from document aggregator 110 and machine learning algorithms applied by search engine 120, identification system 105 may determine a cause or training issue based on the received information.

In step 1014, identification system 105 may generate recommendations and/or treating issue and transmit recommendations or instructions to a client device by generating a GUI in step 1016. For example, in step 1014 identification system 105 may transmit instructions to generate a results user interface like described in connection with FIG. 20. Further, in step 1014 identification system 105 may generate physician recommendations.

Figure 11:
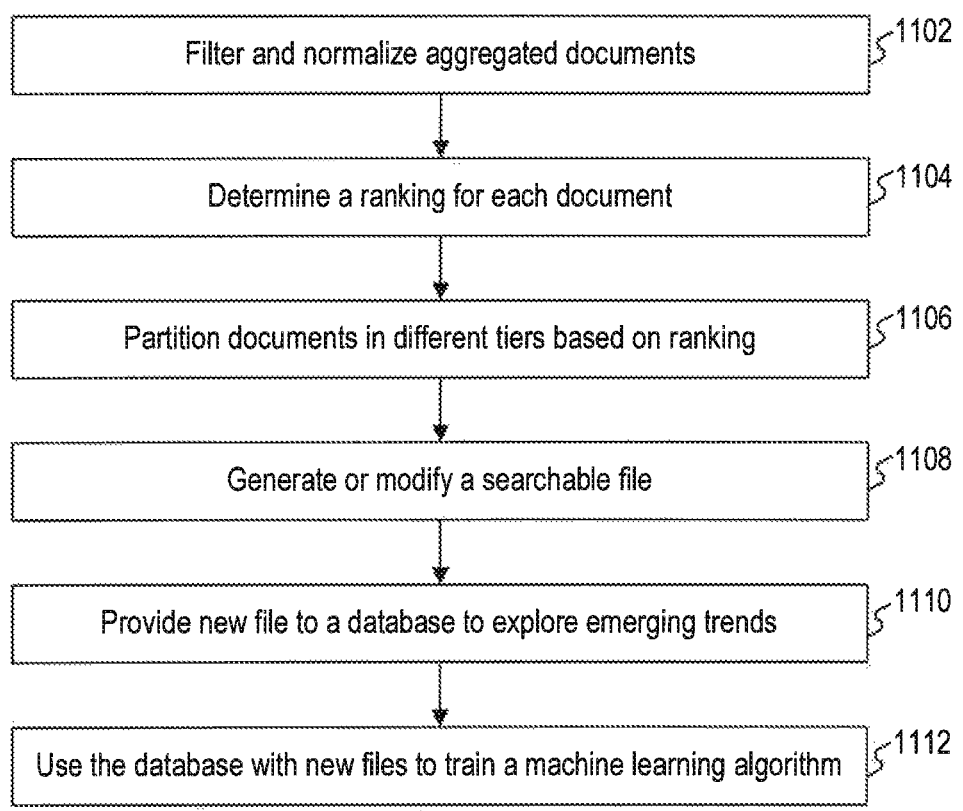
FIG. 11 is an exemplary flow chart illustrating a document machine learning process, in accordance with disclosed embodiments.

FIG. 11 is an exemplary flow chart illustrating a document machine learning process 1100, in accordance with disclosed embodiments. In some embodiments, identification system 105 may perform document machine learning process 1100.

In step 1102, identification system 105 may filter and normalize aggregated documents.

In step 1104, identification system 105 may determine a ranking for each document.

In step 1106, identification system 105 may partition documents in different tiers based on rankings and then generate or modify a searchable file in step 1108.

In step 1110, identification system 105 may provide the new file to databases 180 to explore emerging correlations and trends between medications and complaints to attempt to establish adverse effects of medications.

In step 1112, identification system 105 may incorporate data in a database for training a machine learning algorithm that correlates medications and effects.

In some embodiments, use of AI may identify relevant documents from databases to show relevance of searches based on quality (e.g. evidence class—randomized clinical trial versus case report) or quantity (common versus rare or even problems listed in error) or other (e.g., problem normalization with agent reduction or re-challenge) evidence; search algorithms may learn and adjust to bring back higher and higher levels of relevant results. Also, over time, the AI may prioritize which data it goes to (i.e., FDA versus published journals versus PubMed versus EMR, etc.). For example, the artificial intelligence may use frequency of AEs (Adverse Effects) from FDA drug inserts, post marketing data (FAESR less weighted), principle product summary statement (most complete for FDA filing), reports showing AE (adverse effect) reversal based on dose reduction or stopping medication, randomized clinical trial data highest level of evidence; and group data collected from our user aggregation of feedback. For example, the artificial intelligence may collect data from social networks on complaints to train a model of correlation.

Additionally a search strategy running unprompted in background of EMR may identify links between symptoms/problems/diagnoses/problem lists/text and medications lists and orders (for use immediately by notifying healthcare provider and to create additional database for future searching).

Further, searches may generate new data—keeping searches to use. Integration of these data in combination with the public domain database to a larger proprietary database to run searches against (user can determine which database is best to search for individual purpose).

In some embodiments, process 1100 may create or uncover previously unknown medication/healthcare interactions that are not possible with current approaches. Thus, identification system 105 may become a new data generator. For example, example of new data generated could include medication-efficiency across geographies (outside of the United States) upon people of different generics and socio-economic backgrounds (i.e. access to different types of vitamins, diets and minerals when growing up).

In other embodiments, process 1100 may create novel method to monitor/grade healthcare provider performance (determine compliance with provided recommendations and outcome of avoidable problems).

Figure 12:
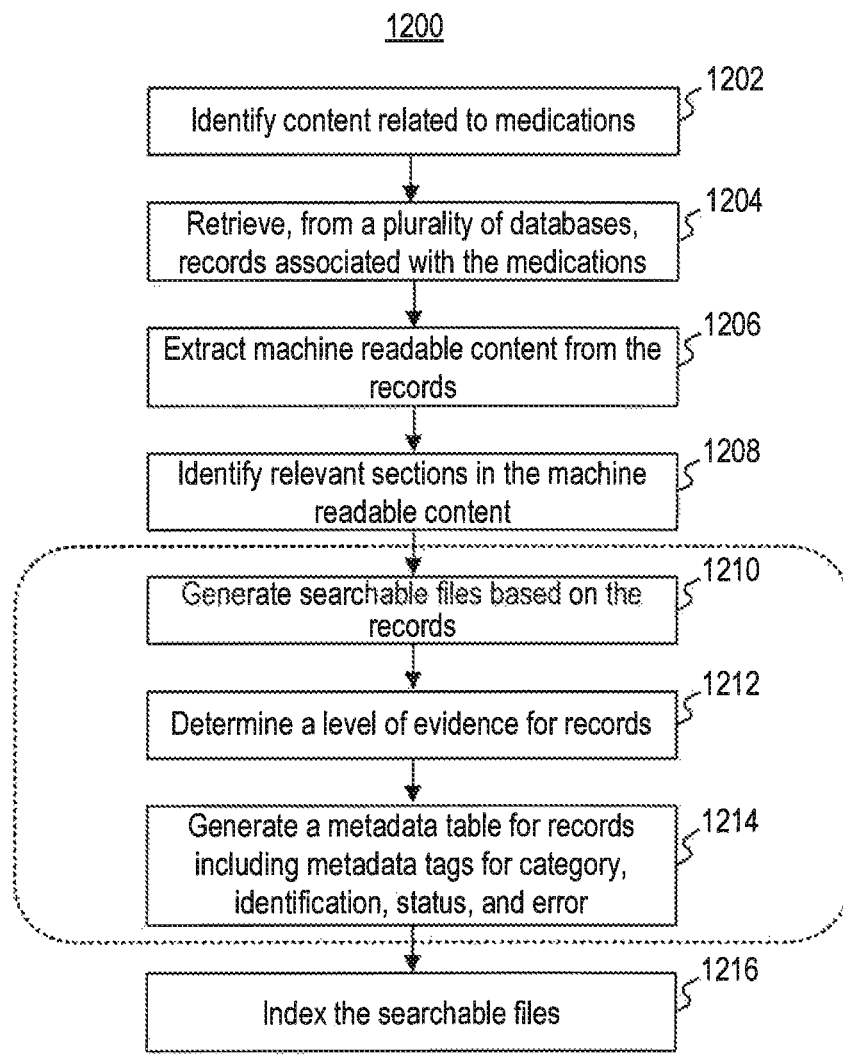
FIG. 12 is an exemplary flow chart illustrating a database generation process, in accordance with disclosed embodiments.

FIG. 12 is an exemplary flow chart illustrating a database generation process 1200, in accordance with disclosed embodiments. In some embodiments, process 1200 may be carried out by identification system 105 (FIG. 1). In such embodiments, process 900 may be carried out by document aggregator 110.

In step 1202, identification system 105 may identify records related to medications of interests. Using key terms rules, identification system 105 may capture records of interests. Records of interest may be retrieved from a plurality of databases in step 1204, aggregating records from multiple sources associated with medications.

In step 1206, identification system 105 may extract machine readable content from the records. For example, identification system 105 may employ optical character recognition (OCR) to extract machine readable content from Portable Document Format (PDF) records. In step 1208, identification system 105 may identify relevant sections in the machine readable content. For example, identification system 105 may identify tables, method sections, and abstract sections with key words that may identify adverse or secondary effects or medications.

In step 1210, identification system 105 may generate searchable files based on the machine readable content extracted from the records. For example, identification system 105 may generate searchable XML files based on the extracted machine readable content. In step 1212, identification system 105 may determine a level of evidence for the retrieved records. For example, using metadata tags, the source of the records, and logic evaluations based on the number of key terms in the record, identification system 105 may determine a level of evidence. The level of evidence may be recorded in a metadata table in step 1214. For example, aggregator processor 230, and more specifically metadata generator 238 (FIG. 2), may generate a table of metadata tags with columns and rows as further described in connection with FIG. 2. In some embodiments, steps 1210, 1212, 1214, may be performed concurrently as new records are being discovered. For example, as web scraper 232 identifies new records, the records may be processed concurrently by metadata generator 238.

In step 1216, identification system 105 may generate an index for searchable files. For example, using features of real-time indexing, dynamic clustering, database integration, NoSQL features, and rich document handling, identification system 105 may generate index files for the records and extracted machine content.

Figure 13:
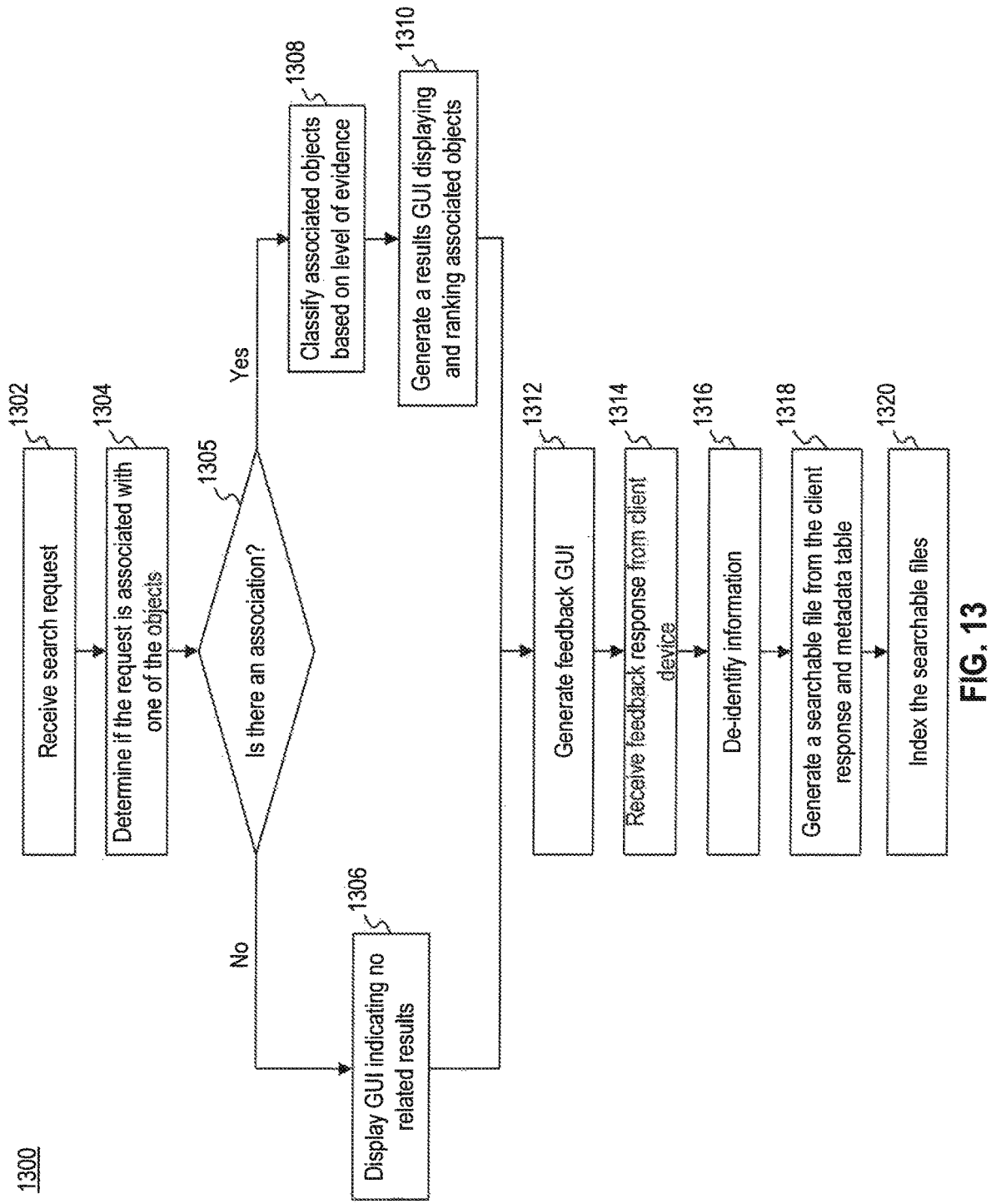
FIG. 13 is an exemplary flow chart illustrating a search request handling process, in accordance with disclosed embodiments.

FIG. 13 is an exemplary flow chart illustrating a search request handling process 1300, in accordance with disclosed embodiments. In some embodiments, process 1300 may be carried out by identification system 105 (FIG. 1). In such embodiments, process 1300 may be carried out by document aggregator 110.

In step 1302, identification system 105 may receive a search request. For example, identification system 105 may receive a request from client devices 150 including a group of medications and a group of problems or symptoms. In some embodiments, the search request may also include genetic information about a patient. For instance, the search request may include a DNA sequence, allele information, and/or pharmacogenomics testing results.

In step 1304, identification system 105 may determine if the request is associated with at least one of the objects in a database or index files. That is, identification system 105 may establish if there is a recorded association between medications and symptoms received in the query. In step 1305, identification system 105 may determine if there is an association. If there is no association between medications and symptoms (step 1305: no), identification system 105 may continue to step 1306 and display a graphical user interface indicating there are no related results. However, if there is an association between medications and symptoms (step 1305: yes), identification system 105 may continue to step 1308 and classify records that associate medications with symptoms based on level of evidence. For example, using metadata tags identification system 105 may determine a ranking for the associated records. Further, in step 1310 identification system 105 may generate a graphical user interface to generate results displaying the records and the ranking for each one of the records, as further described in connection to FIGS. 9 and 20.

In some embodiments, regardless of whether identification system 105 found an association between queried medications and symptoms, identification system 105 may generate a feedback GUI in step 1312. For example, identification system 105 may generate a user interface as described in connection to FIG. 21. In step 1314, identification system 105 may receive the feedback response from client device 150, indicating a user action or medication association. Further, in step 1314 identification system 105 may receive feedback on a treatment result.

In step 1316, identification system 105 may de-identify information, removing sensitive content to be able to aggregate information for trends evaluation. Once information is de-identified, identification system 105 may generate a searchable file in step 1318. Further the searchable file may be indexed in step 1320 for future queries relating medications and symptoms. With this configuration the feedback becomes part of the stored records available to identify correlations between medications and secondary effects.

Figure 14:
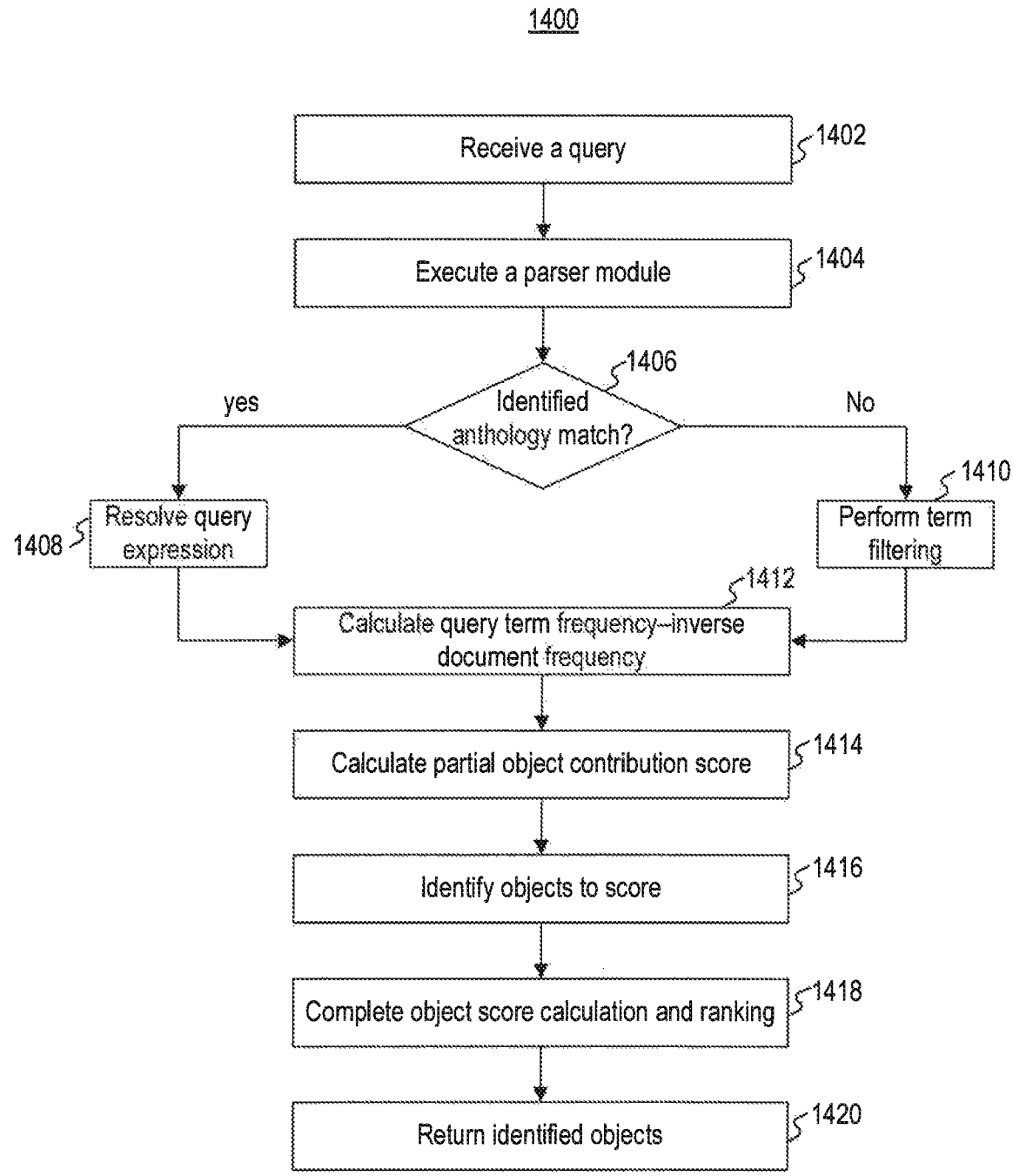
FIG. 14 is an exemplary flow chart illustrating a document searching process, in accordance with disclosed embodiments.

FIG. 14 is an exemplary flow chart illustrating a document searching process 1400, in accordance with disclosed embodiments. In some embodiments, identification system 105 may carry out document searching process 1400. For instance, in some embodiments, document searching process 1400 may be performed by search engine 120.

In step 1402, identification system 105 may receive a query and execute a parser in step 1404.

In step 1406, identification system 105 may determine if there is an anthology match. If identification system 105 determines there is a match (step 1406: yes), identification system 105 may continue to step 1408 and resolve an expression query. However, if identification system 105 determines there is a match (step 1406: yes), identification system 105 may continue to step 1410 and perform a term filtering.

In step 1412, identification system 105 may calculate query term frequency-inverse document frequency and continue to step 1414 to calculate a partial object contribution score.

In step 1416, identification system 105 may identify objects to score and in step 1418 it may complete object score calculation and ranking.

In step 1420, identification system 105 may return identified objects to, for example, client devices 150.

Figure 15:
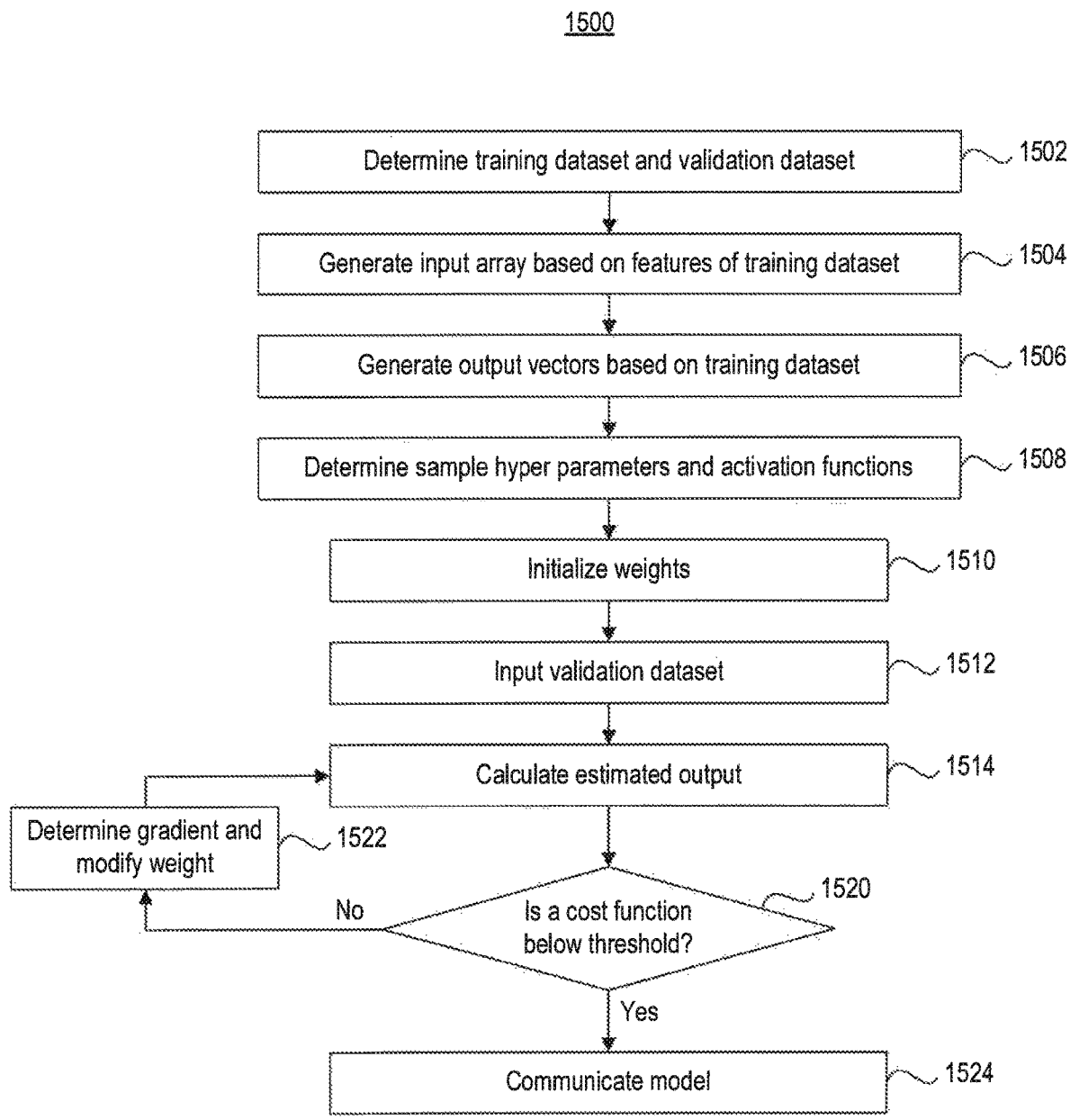
FIG. 15 is an exemplary flow chart illustrating a process for generating a predictive model, in accordance with disclosed embodiments

FIG. 15 is an exemplary flow chart illustrating a process 1500 for generating a predictive model, consistent with disclosed embodiments. Process 1500 may be performed by identification system 105. For example, process 1500 may be executed by machine learning module 346 in engine processor 340 (FIG. 3) and may be configured to generate machine-learning models, such as neural networks.

In step 1502, identification system 105 may determine a training dataset and a validation dataset. Identification system 105 may partition medical records into a training and a validation portions. For example, identification system 105 may receive data including a medication records, such as articles or recall reports. The records may be associated with metadata describing attributes of the record and a level of evidence. Identification system 105 may divide the records and generate two groups, one to train the predictive machine-learning model and a second to validate the model.

In step 1504, identification system 105 may generate an input array based on features of the training dataset. For example, identification system 105 may generate a variable including feature information of transactions and/or records in the training dataset.

In step 1506, identification system 105 may generate output vectors based on metadata of the training dataset. For example, based on the transactions in the training dataset, the identification system may generate a desired output vector making a prediction of, for example, likelihood of correlation between a medication and a problem included in the training dataset.

In step 1508, identification system 105 may determine sample hyper-parameters and activation functions to initialize the model to be created. For example, identification system 105 may select initial hyper-parameters such a number of layers and nodes, and determine whether the network will be fully or partially connected. In addition, in step 1508 identification system 105 may determine the dimensionality of the network and/or determine stacks of receptive field networks. Moreover, in step 1508 identification system 105 may also associate the model with one or more activation functions. For example, identification system 105 may associate the model with one or more sigmoidal functions. In step 1510 identification system 105 may initialize weights for synapsis in the network.

In step 1512, identification system 105 may input a validation dataset in the model. For example, identification system 105 may apply the input array based on features of training dataset of step 1504 to calculate an estimated output in step 1514 and a cost function. In step 1520, identification system 105 may determine whether the cost function is below a threshold of required accuracy, which may be specified by the user. If identification system 105 determines that the cost function is not below a threshold and the required accuracy has not being achieved, identification system 105 may continue to step 1522 and modify model parameters. For example, when generating a neural network, in step 1522 identification system 105 may determine a gradient to modify weights in synapses or modify the activation functions in the different nodes. However, if the cost function if below a threshold (step 1520: yes), identification system may accept and communicate the model in step 1524.

Figure 16:
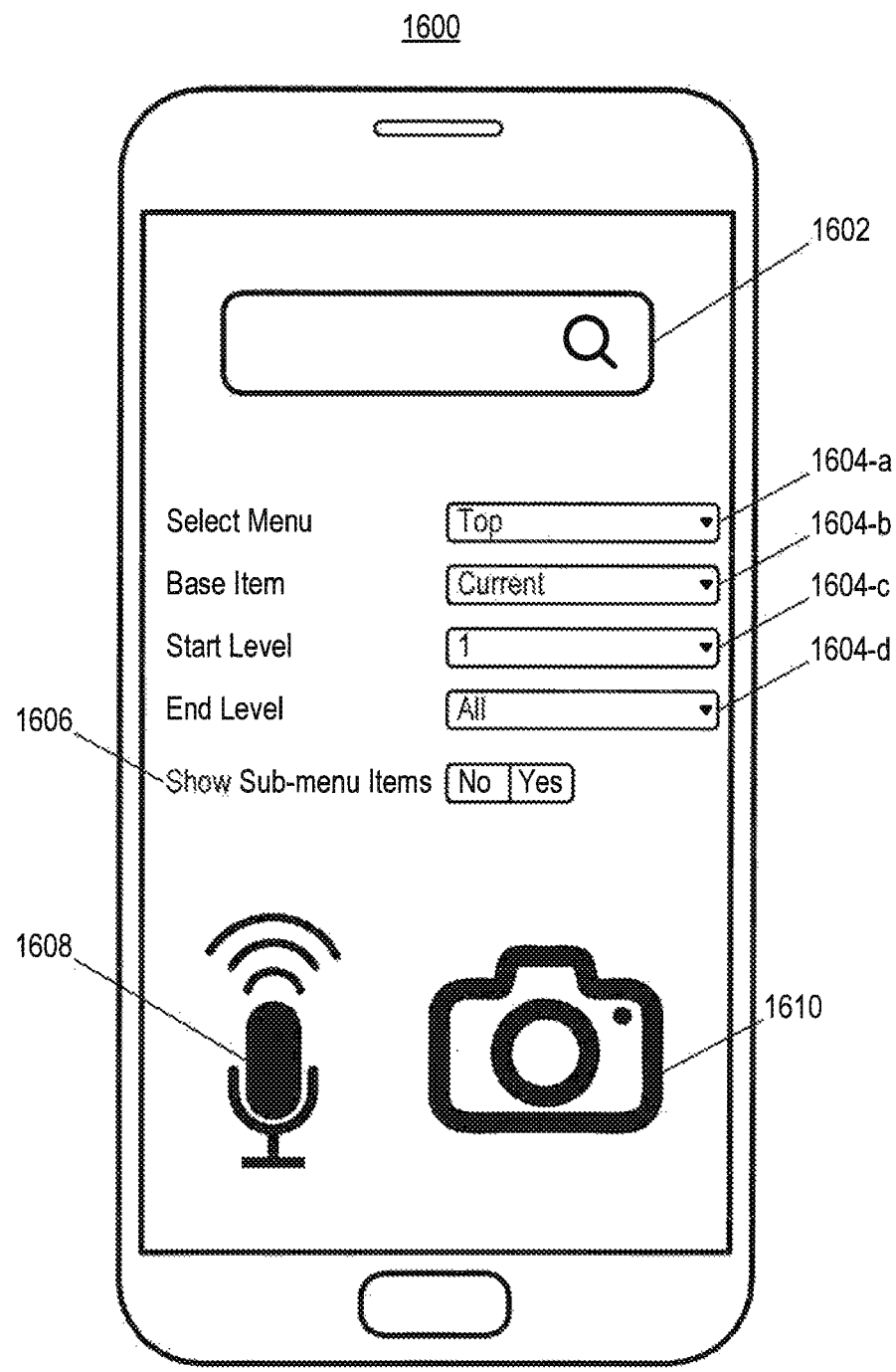
FIG. 16 is an exemplary graphical user interface for receiving a document query, in accordance with disclosed embodiments.

FIG. 16 is an exemplary user interface 1600, in accordance with disclosed embodiments. In some embodiments, identification system 105 may generate instructions to display user interface 1600 in client devices 150.

User interface 1600 may include a search bar 1602, a plurality of drop-down menus 1604, and switch buttons 1606. In addition, user interface 1600 may include a microphone icon 1608 and a picture icon 1610.

As disclosed in connection with FIGS. 17-21, the disclosed identification system 105 may be implemented as a desktop application. However, in other embodiments identification system 105 may be available as an app for both iOS and Android mobile systems.

In some embodiments, identification system 105 may receive two key items as input, a complaint and a medication. In such embodiments, the practitioner may initially enter only one complaint using a graphical user interface. The more sophisticated or precise the complaint wording, the more accurate the search may be conducted by identification system 105. Identification system 105 may use MedDRA (Medical Dictionary for Regulatory Activities). MedDRA is a database that presents organized terminology that is maintained with addition of terms as new medical knowledge grows. It is under the governance of the ICH (International Council for Harmonisation of Technical Requirements for Pharmaceuticals for Human Use (ICH) a non-profit association) MedDRA Management Committee. It is used across regulatory agencies as well as for clinical trials. User interface 1600 may be configured to enter free text that is 'auto-coded' to a MedDRA preferred term (PT), with options displayed in a drop-down menu, from which the provider can select the desired PT. The actual search in identification system 105 may be conducted on the input PT as well as related lower level terms (LLTs) associated with that PT. For example, identification system 105 may amplify the practitioner's diagnostic considerations to create a more comprehensive search.

Moreover, other embodiments of user interface 1600 may allow the entry of multiple free text, and utilize both MedDRA dictionary coding as well as learnings from within the product to optimize selected PTs. Yet other embodiments of user interface 1600 may allow entry of non-medical terms that might be used by individuals without medical knowledge.

Additional or alternative functionality of user interface 1600 may include the ability to speak the complaint rather than enter free text, and the ability to capture what the patient says is the chief complaint, live or by voice recording. For example, a user may click in microphone icon 1608 to record the complaint.

User interface 1600 may be configured to facilitate creation of the proprietary database, so practitioners may be given the option to add additional terms (akin to LLTs) to the search. Initially, these secondary terms may be tracked for associations with medications. Other embodiments may include these terms, collected from prior searches, in the actual search.

Further, is some embodiments users may enter medications via free text to an 'auto-coding' dictionary using the World Health Organization (WHO) Drug Global dictionary for terms and categories of medications (and WHO standardized medication groupings). For example, WHO Drug Global has become the global standard and the most comprehensive and actively used medication reference dictionary in the world.

Drop-down boxes, such as drop-down menus 1604 may allow the provider to select the correct medications, whether by brand or generic name.

In some embodiments, user interface 1600 is configured to capture voice reading of the medication names, or to utilize a photo of the medication itself or the bar code of the prescription label. In addition, user interface 1600 may allow a user to import medication data from an EMR/EHS system and may be a future function. Other functionality of user interface 1600 may include the ability to capture manufacturer, production version, and source geography for point of origin for the medications from pharmaceutical systems.

In some embodiments, user interface 1600 may include a Design/Format of screen appearance with drop-down menus for searches (that introduce WHO and MeDRA terms); or may include results with URL/summary tables or graphs classified by class/quality of evidence. Alternatively, or additionally, user interface 1600 may include a design/Format for healthcare provider feedback to provide outcome and reason (e.g., symptom resolution after agent reduction or withdrawal; and/or re-challenge with agent) of whether problem is unrelated.

Figure 17:
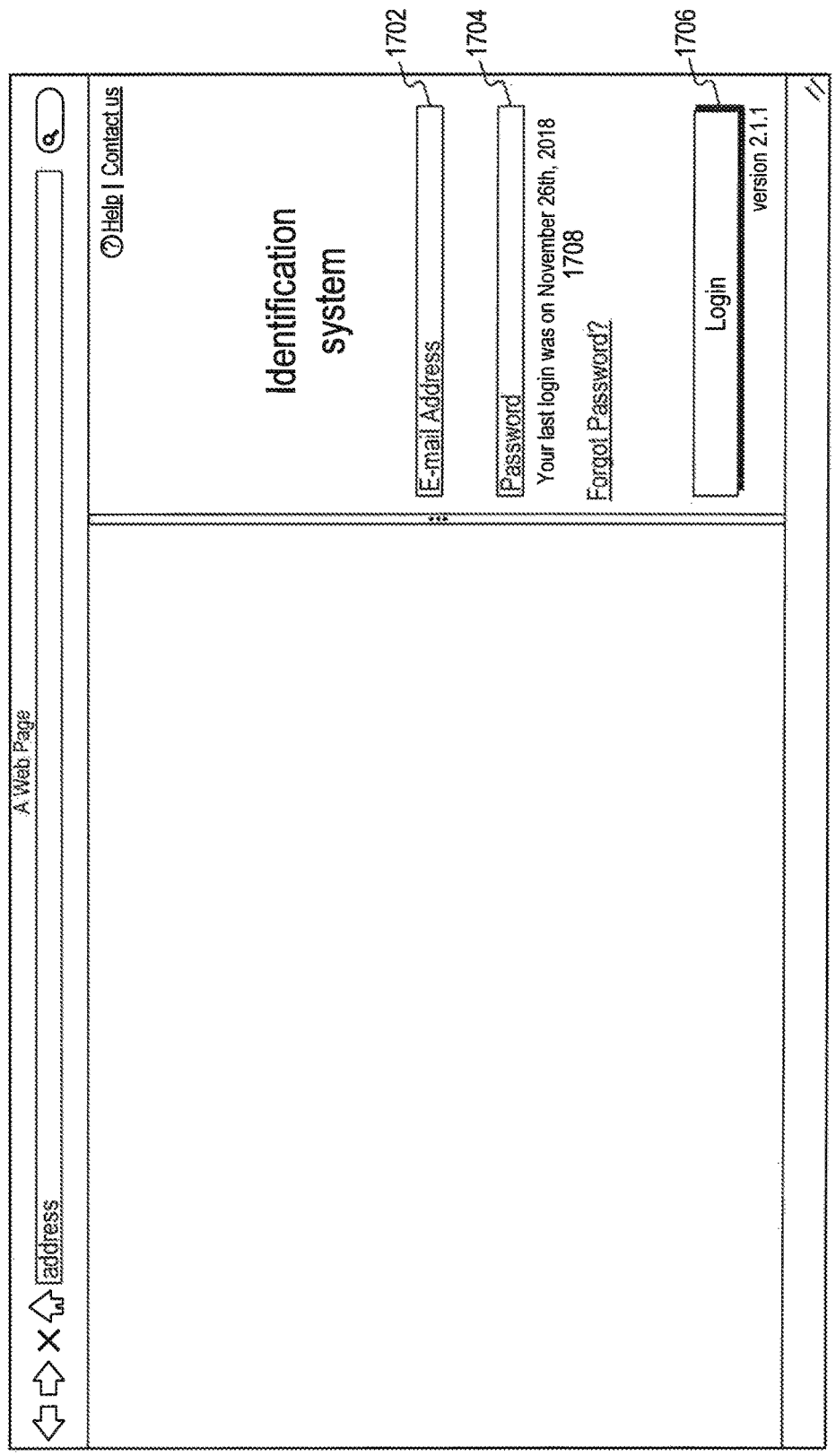
FIG. 17 is an exemplary graphical user interface for accessing an identification system, in accordance with disclosed embodiments.

FIG. 17 is an exemplary graphical user interface 1700 for accessing an identification system, in accordance with disclosed embodiments. In some embodiments, identification system 105 may generate instructions to display user interface 1700 in client devices 150.

User interface 1700 may be displayed when a client device attempts to access identification system 105. For example, user interface 1700 may be transmitted to client devices 150 when client devices 150 request a URL associated with identification system 105.

User interface 1700 may include an email text box 1702, a password text box 1704, and a login button 1706. Information inputted in the text boxes may be used by identification system 105, and particularly by search engine 120, to authenticate a user and determine its level of access.

Figure 18:
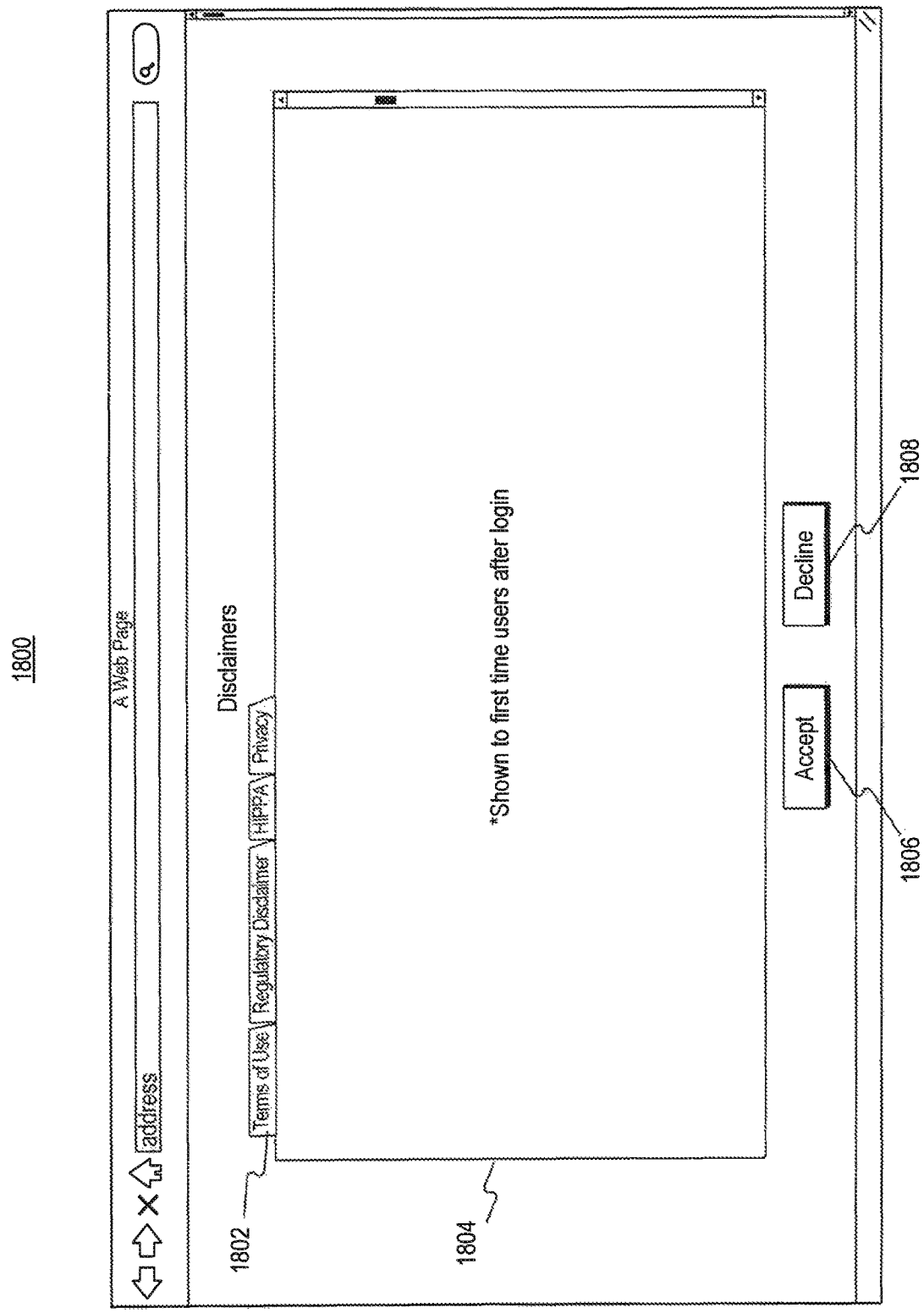
FIG. 18 is an exemplary graphical user interface for displaying disclaimers, in accordance with disclosed embodiments.

FIG. 18 is an exemplary graphical user interface 1800 for displaying disclaimers, in accordance with disclosed embodiments. In some embodiments, identification system 105 may generate instructions to display user interface 1800 in client devices 150.

User interface 1800 may be displayed as the first page shown once a user is authenticated. User interface 1800 may include a disclaimer window 1804, which may display tabs 1802 for regulatory disclaimer, HIPPA notices, or privacy notices, using tabs. Further, user interface 1800 may include accept button 1806 and decline button 1808.

Figure 19:
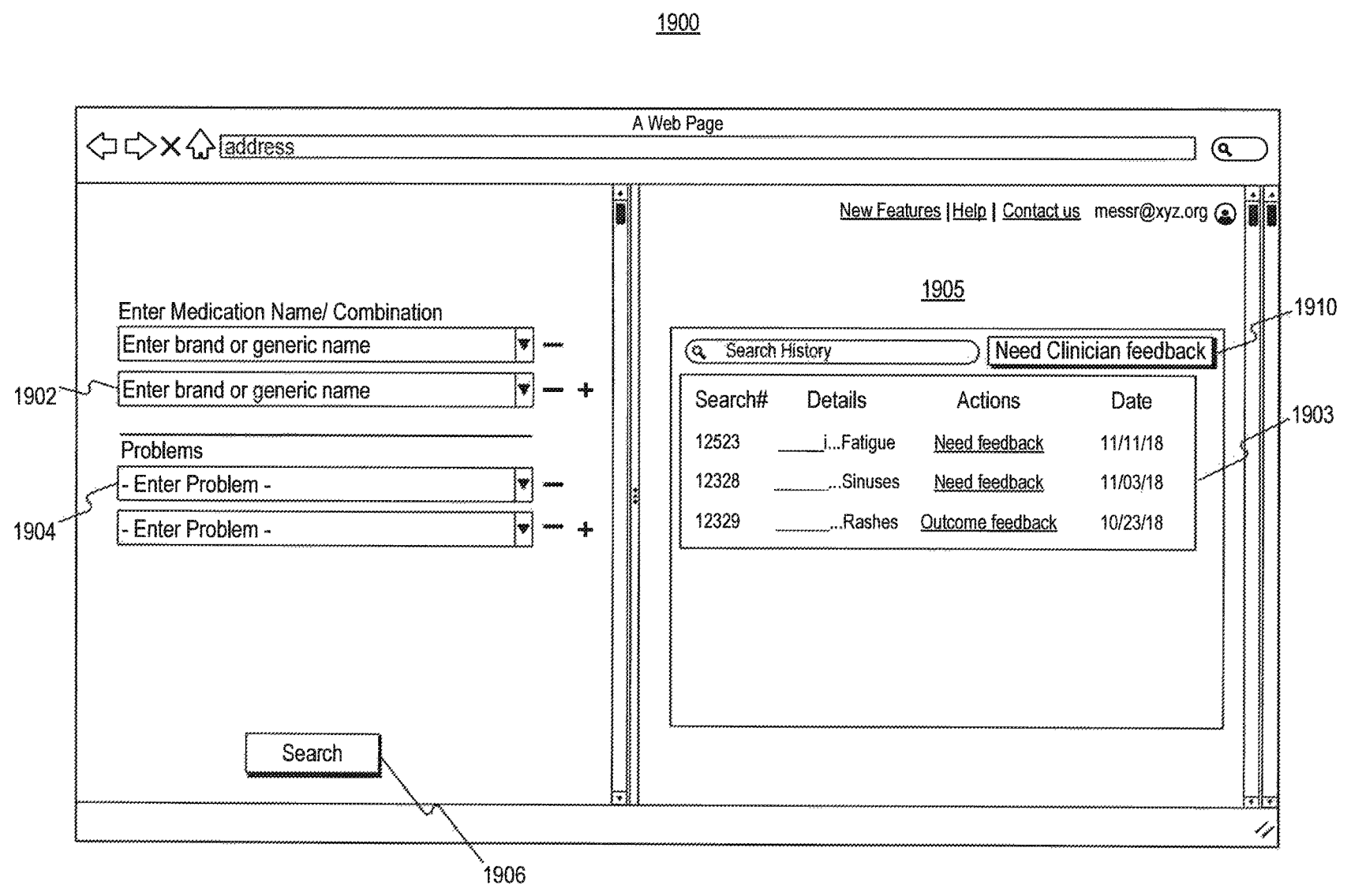

FIG. 19 is an exemplary graphical user interface 1900 for search query input, in accordance with disclosed embodiments. In some embodiments, identification system 105 may generate instructions to display user interface 1900 in client devices 150.

User interface 1900 may be displayed in client devices to collect information for a search query. User interface 1900 may include a plurality of medication selections 1902 to collect medication names or combinations. User interface 1900 may also include a plurality of problem selections 1904 to collect symptoms, problems, or effects that the user wants to query. Further, user interface 1900 may include a search button 1906 to send queries to identification system 105. In some embodiments, when a user interacts with search button 1906 the following user interface that is displayed in a client device 150 is similar to the user interface described in connection to FIG. 20.

In some embodiments, user interface 1900 may include a search history window 1905 including past searches. Search history window 1905 may include a listing of previous searches 1903 and a feedback button 1910. In certain embodiments, when a user interacts with feedback button 1910 the following user interface that is displayed in a client device 150 is similar to the user interface described in connection to FIG. 21.

Figure 20:
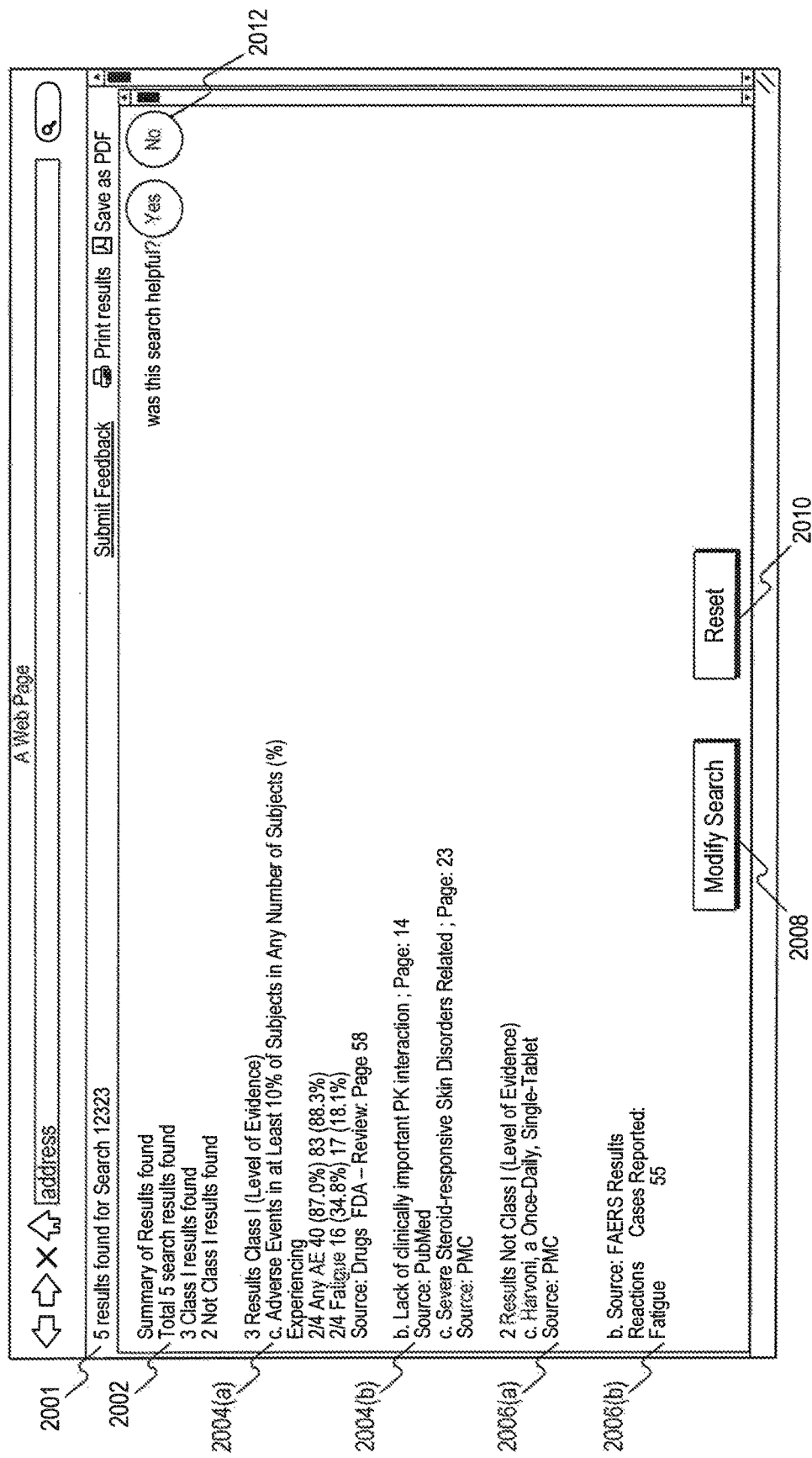
FIG. 20 is an exemplary graphical user interface for displaying results, in accordance with disclosed embodiments.

FIG. 20 is an exemplary graphical user interface 2000 for displaying results, in accordance with disclosed embodiments. In some embodiments, identification system 105 may generate instructions to display user interface 2000 in client devices 150.

User interface 2000 may be displayed in client devices to report results from a search query. User interface 2000 may include a results header 2001 and a summary of results 2002 indicating the number of records associated with the query and the ranking of the identified records. User interface 2000 may also include categorized listings 2004. For example, user interface may include a class 1 categorized listing 2004(a) displaying results of the highest level of evidence. Class 1 categorized listing 2004(a) may include the number of records and a statistical analysis of the probability of correlation between medications and symptoms. Class 2 categorized listing 2004(b) may include records with lower levels of evidence but display similar information about associations between medications and symptoms.

In some embodiments, user interface 2000 may also include additional listings 2006, including records that have not been categorized in a no results listing 2006(a) and/or records from alternative listings 2006(b) that are not classifiable in the classes of categorized listings 2004.

User interface 2000 may also include a modify search button 2008, which may return the user to user interface 1900 (FIG. 19) and a reset button 2010. In addition, user interface 2000 may include survey buttons 2012 to collect information from users.

In some embodiments, user interface 2000 may display search results ranked by level of evidence with the highest class of evidence displayed first as Class I and rest as Class II-IV. In such embodiments, user interface 2000 may include text labels that informs users of associations found between the medication and the medication. For example, identification system 105 may include text labels such as "found association between the medication and problem" or "no association between the medication and the problem." Further, in some embodiments user interface 2000 may display any new FDA warnings related to the medication under the summary, followed by all the LoE results. Further, user interface 2000 may include search results found for e.g. Summary of Results found—Total 5 search results found, 3 "Class I" results found and 2 "Class II-IV" results found. In such embodiments, identified records with relevant results (Tables and results data for specific problem) may be displayed, with page number, and URL for each table.

FIG. 21 is an exemplary graphical user interface 2100 for feedback input, in accordance with disclosed embodiments. In some embodiments, identification system 105 may generate instructions to display user interface 2100 in client devices 150.

User interface 2100 may include checkboxes to collect feedback from the user. The checkboxes may include options to describe the action taken with medication, outcome of the problem, and improvements. For example, user interface 2100 may include action checkboxes 2102, outcome checkboxes 2104, and condition checkboxes 2106. In addition, user interface 2100 may include a comments textbox 2108 and a submit feedback button 2110.

Using user interface 2100 users can provide feedback directly on the search results. For example, using a floating (flashing) icon in search history window 1905 to take action on all search results. A user may see a notification icon, in the search history section, when they log into the application, which will indicate that they can provide feedback and take the user to user interface 2100.

In some embodiments, identification system 105 may include feedback auto-reminders that may be sent in the form of email to the user, which may take user back to application for the feedback. In such embodiments, identification system 105 may be configured so each reminder may be resent a maximum of three times (for each time point), if the user has not provided the feedback.

Feedback collected with user interface 2100 may include outcome of action, medication cessation, or reduction. Further, identification system 105 program user interface 2100 to provide reminders to be sent collectively as a single email for any or all feedback depending on the time period.

Feedback collected with user interface 2100 may be tracked by the Case Number and related to the User who triggered the search. It may consist of the following questions and options for the user to choose from: Action taken with Med? Options with the check box Stopped, reduced and unchanged; outcome of the problem. Options with the check box Improved and worsened; if therapy changed, how long till condition improved. With these questions in user interface 2100, identification system 105 may collect information from users to enhance information in the database and determine correlations between medications and symptoms.

Another aspect of the disclosure is directed to a non-transitory computer-readable medium storing instructions that, when executed, cause one or more processors to perform the methods, as discussed above. The computer-readable medium may include volatile or non-volatile, magnetic, semiconductor, tape, optical, removable, non-removable, or other types of computer-readable medium or computer-readable storage devices. For example, the computer-readable medium may be the storage unit or the memory module having the computer instructions stored thereon, as disclosed. In some embodiments, the computer-readable medium may be a disc or a flash drive having the computer instructions stored thereon.

It will be apparent to those skilled in the art that various modifications and variations can be made to the disclosed system and related methods. Other embodiments will be apparent to those skilled in the art from consideration of the specification and practice of the disclosed system and related methods. It is intended that the specification and examples be considered as exemplary only, with a true scope being indicated by the following claims and their equivalents.

Moreover, while illustrative embodiments have been described herein, the scope thereof includes any and all embodiments having equivalent elements, modifications, omissions, combinations (e.g., of aspects across various embodiments), adaptations and/or alterations as would be appreciated by those in the art based on the present disclosure. For example, the number and orientation of components shown in the exemplary systems may be modified. Further, with respect to the exemplary methods illustrated in the attached drawings, the order and sequence of steps may be modified, and steps may be added or deleted.

Thus, the foregoing description has been presented for purposes of illustration only. It is not exhaustive and is not limiting to the precise forms or embodiments disclosed. Modifications and adaptations will be apparent to those skilled in the art from consideration of the specification and practice of the disclosed embodiments.

The claims are to be interpreted broadly based on the language employed in the claims and not limited to examples described in the present specification, which examples are to be construed as non-exclusive. Further, the steps of the disclosed methods may be modified in any manner, including by reordering steps and/or inserting or deleting steps.

What is claimed is:

1. A system for identifying side effects of medications comprising:
one or more processors; and
a storage medium storing instructions that, when executed, configure the one or more processors to perform operations comprising:
retrieving a plurality of records associated with medications from a plurality of servers;
extracting machine readable content from each of the plurality of records;
identifying portions of the machine readable content that are associated with side effects or adverse events of medications;
aggregating the identified portions of the machine readable content in a database using markup language files;
determining a level of evidence for each of the plurality of records based on corresponding record sources through a class categorization, the level of evidence categorizing each of the plurality of records in at least one of:
a first category associated with masked randomized clinical trial sources,
a second category associated with at least one of unmasked randomized clinical trial sources or open label trials sources,
a third category associated with clinical case-control studies sources, and
a fourth category associated with clinical event reporting sources;
associating each of the plurality records with metadata tags comprising a tag indicative of at least one of the first to fourth categories, a tag indicative of medication identification, and a tag indicative of file status;
generating index files mapping the markup language files, the metadata tags, and the medications;
receiving a search query from a client device, the search query comprising at least one medication;
identifying a subset of the plurality of records associated with the at least one medication using the index files, wherein the subset comprises records of the at least one medication, records identifying side effects or adverse events of the at least one medication, and records associated with at least one of the four categories; and
transmitting, to the client device, the identified subset ranked according to the level of evidence.

2. The system of claim 1 further comprising,
transmitting, to the client device, instructions to display a feedback graphical user interface after transmitting the subset;
receiving, from the client device, feedback information for the at least one medication;
determining the level of evidence for the feedback information;
associating the feedback information with metadata tags indicating the corresponding level of evidence; and
generating index files mapping the feedback information.

3. The system of claim 2, wherein
the feedback information comprises at least one of a client action, an outcome result, or a client search content.

4. The system of claim 1, further comprising:
partitioning the markup language files and the metadata tags files into validation and training datasets;
generating a predictive model using the training dataset;
determining an accuracy of the predictive model using a validation dataset; and
providing a recommendation to the client device for the at least one medication based on the predictive model.

5. The system of claim 4, wherein the predictive model comprises at least one of a random forest or a convolutional neural network.

6. The system of claim 4, wherein the predictive model comprises a clustering technique that associates symptoms with medications across one or more healthcare user networks.

7. The system of claim 1, wherein aggregating the identified portions of the machine readable content comprises, for each one of the plurality of records:
identifying a section within the machine readable content related to side effects;
identifying a table format within the section;
extracting data contained within the table format; and
storing data contained within the table format in a markup language file.

8. The system of claim 7, wherein aggregating the identified portions of the machine readable content further comprises:
identifying keywords in the machine readable content indicating at least one of: side effects, adverse events, or complications; and
extracting sections from the machine readable content with the identified keywords.

9. The system of claim 8, wherein:
the plurality of records comprise PDF files;
extracting sections in the machine readable content with the identified keywords comprises executing an OCR; and
storing data contained within the table format comprises, for each table format:
determining if the table format includes adverse events based on a table header or table footer; and
storing data contained within the table format in the markup language file when determining the table format includes adverse events.

10. The system of claim 7, wherein associating the plurality of records with metadata tags comprises generating at least one classification tag based on a group of keywords found in the corresponding record.

11. The system of claim 1, wherein:
transmitting the identified subset comprises transmitting instructions to generate a result user interface in the client device, the results user interface comprising a button, and
the one or more processor is further configured to perform operations comprising:
receiving from the client device an indication of interaction with the button;
transmitting instructions to generate a feedback user interface comprising one or more check boxes;
receiving from the client device a feedback message; and
generating index files mapping the feedback information.

12. The system of claim 1, wherein the search query comprises symptoms auto coded to MedDRA terms.

13. The system of claim 1, wherein associating the plurality of records with metadata tags comprises:
for each of the plurality of records:
identifying a method section and an abstract section within the machine readable content;
identifying a plurality of keywords matching a list of predetermined terms; and
categorizing the corresponding record in a level of evidence category based on a score determined on a combination of the plurality of keywords.

14. The system of claim 13, wherein records in the plurality of records are deleted when the level of evidence is below a minimum category score.

15. The system of claim 1, wherein associating the plurality of records with metadata tags comprises generating a metadata table comprising rows for each one of the plurality of records and a plurality of columns including identification tags, file tags, status tags; and error tags.

16. The system of claim 15, wherein:
the search query comprises information of a patient; and
receiving the search query comprises:
standardizing search categories using a dictionary entry;
retrieving electronic healthcare records associated with the patient;
determining an association between a condition and a medication; and
generating recommendations to transmit to the client device.

17. The system of claim 16, further comprising:
determining an emerging association between a medication and a symptom based on search queries received from a plurality of client devices.

18. The system of claim 1, wherein:
extracting machine readable content comprises converting image files into text files and employing a Java content detection framework configured to parse the text files and related metadata; and
the metadata tags further comprise an OCR error tag, an index error tag, and an Apache error tag.

19. A non-transitory computer-readable medium storing instructions that, when executed by a processor, cause the processor to operate a system for identifying side effects of medications, the operations comprising:
retrieving a plurality of records associated with medications from a plurality of servers;
extracting machine readable content from each of the plurality of records;
identifying portions of the machine readable content that are associated with secondary effects of medications;
aggregating the identified portions of the machine readable content in a database using markup language files;
determining a level of evidence for each of the plurality of records based on corresponding record sources through a class categorization, the level of evidence categorizing each of the plurality of records in at least one of:
a first category associated with masked randomized clinical trial sources;
a second category associated with at least one of unmasked randomized clinical trial sources or open label trials sources;
a third category associated with clinical case-control studies sources; and
a fourth category associated with clinical event reporting sources;
associating each of the plurality records with metadata tags comprising a tag indicative of at least one of the first to fourth categories, a tag indicative of medication identification, and a tag indicative of file status;
generating index files mapping the markup language files, the metadata tags, and the medications;
receiving a search query from a client device, the search query comprising at least one medication;
identifying a subset of the plurality of records associated with the at least one medication using the index files, wherein the subset comprises records of the at least one medication, records identifying side effects or adverse events of the at least one medication, and records associated with at least one of the four categories; and transmitting, to the client device, the identified subset ranked according to the level of evidence.

20. A computer-implemented method for identifying side effects of medications, the method comprising:

retrieving a plurality of records associated with medications from a plurality of servers;

extracting machine readable content from each of the plurality of records;

identifying portions of the machine readable content that are associated with secondary effects of medications;

aggregating the identified portions of the machine readable content in a database using markup language files;

determining a level of evidence for each of the plurality of records based on corresponding record sources through a class categorization, the level of evidence categorizing each of the plurality of records in at least one of:

a first category associated with masked randomized clinical trial sources;

a second category associated with at least one of unmasked randomized clinical trial sources or open label trials sources;

a third category associated with clinical case-control studies sources; and a fourth category associated with clinical event reporting sources;

associating each of the plurality records with metadata tags comprising a tag indicative of at least one of the first to fourth categories, a tag indicative of medication identification, and a tag indicative of file status;

generating index files mapping the markup language files, the metadata tags, and the medications;

receiving a search query from a client device, the search query comprising at least one medication;

identifying a subset of the plurality of records associated with the at least one medication using the index files, wherein the subset comprises records of the at least one medication, records identifying side effects or adverse events of the at least one medication, and records associated with at least one of the four categories; and transmitting, to the client device, the identified subset ranked according to the level of evidence.

* * * * *